ис012196746B2

United States Patent
Kumar et al.

(10) Patent No.: US 12,196,746 B2
(45) Date of Patent: Jan. 14, 2025

(54) **ENHANCED CHEMILUMINESCENT ENZYME-LINKED IMMUNOSORBENT ASSAY FOR DETECTION OF ANTIBODIES AGAINST *BABESIA microti***

(71) Applicant: The U.S.A., as represented by the Secretary, Department of Health and Human Services, Silver Spring, MD (US)

(72) Inventors: Sanjai Kumar, Potomac, MD (US); Nitin Verma, Germantown, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 18/187,241

(22) Filed: Mar. 21, 2023

(65) Prior Publication Data

US 2023/0266306 A1 Aug. 24, 2023

Related U.S. Application Data

(63) Continuation of application No. 16/761,034, filed as application No. PCT/US2018/058723 on Nov. 1, 2018, now Pat. No. 11,639,930.

(60) Provisional application No. 62/580,588, filed on Nov. 2, 2017.

(51) Int. Cl.
| | |
|---|---|
| *G01N 33/00* | (2006.01) |
| *C07K 14/44* | (2006.01) |
| *C12N 15/10* | (2006.01) |
| *G01N 33/543* | (2006.01) |
| *G01N 33/569* | (2006.01) |

(52) U.S. Cl.
CPC ....... *G01N 33/54306* (2013.01); *C07K 14/44* (2013.01); *C12N 15/1096* (2013.01); *G01N 33/56905* (2013.01); *C07K 2319/00* (2013.01); *G01N 2469/20* (2013.01)

(58) Field of Classification Search
CPC ....... G01N 33/54306; G01N 33/56905; C07K 14/44; C12N 15/1096
See application file for complete search history.

(56) References Cited

U.S. PATENT DOCUMENTS

| | | |
|---|---|---|
| 6,183,976 B1 | 2/2001 | Reed et al. |
| 6,214,971 B1 | 4/2001 | Reed et al. |
| 6,569,433 B1 | 5/2003 | Reed et al. |
| 8,178,310 B2 | 5/2012 | Hoey et al. |
| 8,283,124 B2 | 10/2012 | Birkenmeyer et al. |
| 2002/0169136 A1 | 11/2002 | Reed et al. |
| 2013/0244258 A1 | 9/2013 | Erwin, III et al. |
| 2015/0218657 A1 | 8/2015 | Wang et al. |
| 2021/0181190 A1 | 6/2021 | Kumar et al. |

FOREIGN PATENT DOCUMENTS

| | | |
|---|---|---|
| EP | 0834567 | 4/1998 |
| WO | WO 99/29869 | 6/1999 |
| WO | WO 00/60090 | 10/2000 |
| WO | WO 2013/059795 | 4/2013 |
| WO | WO 2017/100598 | 6/2017 |

OTHER PUBLICATIONS

Edelman et al. 2001 (Degeneracy and complexity in biological systems; PNAS 98(24): 13763-13768) (Year: 2001).*
Cornillot et al. 2012(Sequencing of the smallest Apicomplexan genome from the human pathogen Babesia microti; Nucleic Acids Research 40(18): 9102-9114). (Year: 2012).*
Bloch et al., "A Prospective Evaluation of Chronic *Babesia microti* Infection in Seroreactive Blood Donors," *Transfusion*, vol. 56:1875-1882, 2016.
Cornillot et al., "A Targeted Immunomic Approach Identifies Diagnostic Antigens in the Human Pathogen *Babesia microti*," *Transfusion*, vol. 56:2085-2099, 2016.
Houghton et al., "Identification of *Babesia microti*-specific Immunodominant Epitopes and Development of a Peptide EIA for Detection of Antibodies in Serum," *Transfusion*, vol. 42: 1488-1496, 2002.
International Search Report and Written Opinion of PCT/US2018/058723, mailed Mar. 20, 2019.
Levin et al., "Determination of *Babesia microti* Seroprevalence in Blood Donor Populations using an Investigational Enzyme Immunoassay," *Transfusion*, vol. 54:2237-2244, 2014.
Levin et al., "Serologic Screening of United States Blood Donors for *Babesia microti* using an Investigational Enzyme Immunoassay," *Transfusion*, vol. 56:1866-1874, 2016.
Meredith et al., "Technologies for Detection of *Babesia microti*: Advances and Challenges," *Pathogens*, vol. 10:1563, 2021.
Silva et al., "Genome-wide Diversity and Gene Expression Profiling of *Babesia microti* Isolates Identify Polymorphic Genes that Mediate Host-Pathogen Interactions," *Sci. Rep.*, vol. 6:35284, 2016.
UniParc Accession No. UPI000274BDEB, Oct. 3, 2012 (1 page).
Vannier et al., "Babesiosis," *Infect. Dis. Clin. North Am.*, vol. 29:357-370, 2015.

* cited by examiner

*Primary Examiner* — Mary Maille Lyons
(74) *Attorney, Agent, or Firm* — Klarquist Sparkman, LLP

(57) ABSTRACT

Identification of immunodominant *Babesia microti* antigens using genome-wide immunoscreening is described. Candidate antigens were screened against sera from patients with clinical babesiosis. Also described are diagnostic assays with high sensitivity and specificity for detecting *B. microti*-specific antibodies in patient samples using the identified immunodominant antigens.

17 Claims, 4 Drawing Sheets

Specification includes a Sequence Listing.

SEQUENCE LISTING

```
Sequence total quantity: 10
SEQ ID NO: 1            moltype = DNA  length = 1128
FEATURE                 Location/Qualifiers
source                  1..1128
                        mol_type = other DNA
                        organism = Babesia microti
SEQUENCE: 1
gctaagcaga ctttcatcaa aaacaaatct ctcactaatc ctggcgtgga caatccgaac    60
ttatctgaag gagtcgttcc atccgatgaa catatttctt cgcaatccca aatccaactt   120
ttgagcccac tagcaacacc atttcaagtg atacatctca accaatcaac caaccaacca   180
atcaaccaac caaccaatca accagtcaac caaccaacca accaatcaac caaccaacca   240
accaatcaac caaccaacca accaaccaac caatcaacca accaaccaac caatcaacca   300
aacaaccaac caaccaacca atcaaccaaa caaccaacca accaaccagt caaccaatca   360
accaaccaac caatcaacca accaaccaaca caaccaaccaa accaaccaat caaccaatca   420
accaaacaac caaccaacca accagtcaac caaccaaaca accagtcaac caaccaacca   480
accaatcaac caatcaacca aacaaccaat caaccaaaca accaaccaac cagtcaacca   540
accaatcaac cagtcaacca accaatcaac cagtcaacca accaaacaac caatcagtca   600
accaaccaac caatcaacca atcaaccaaa caaccaacca aacaaccaac caaccaacca   660
aacaaccaaa caaccaacca atcaaccagt caaccaacca aacaaccaat cagtcaacca   720
atcaaccaac caaacaatat aatgggagat aagcggggcc tcaaaggcgc tgaaaccatg   780
agtcctgcgc ccctattcgt tgaagttgac atcctgaaag attctttgga tagtaactta   840
gaagtattat atcaagttag tgttaatgct attatgtttg tccgcgtcgc tagaaacatg   900
gcctcaaaca tcataattaa aagtgtaaag gttggagaag atattttgta tttaaatgat   960
cgaagacttg acctaattct tgaatttaca gttacttctc aacagggttt ccatatgagg  1020
atctacaata atgatgatcg tacggagaat ggtgttatcg gctttctttg ttctttcata  1080
gttgcagatc atattcctaa gtggtacaat ccacctaact cacgccgt               1128

SEQ ID NO: 2            moltype = AA  length = 376
FEATURE                 Location/Qualifiers
source                  1..376
                        mol_type = protein
                        organism = Babesia microti
SEQUENCE: 2
AKQTFIKNKS LTNPGVDNPN LSEGVVPSDE HISSQSQIQL LSPLATPFQV IHLNQSTNQP    60
INQPTNQPVN QPTNQSTNQP TNQPTNQPTN QSTNQPTNQP NNQPTNQSTK QPTNQPVNQS   120
TNQPINQSTK QPNNQPINQS TKQPTNQPVN QPNNQSTNQP TNQPINQTTN QPNNQPTSQP   180
TNQPVNQPIN QSTNQTTNQS TNQPINQSTK QPTKQPTNQP NNQTTNQSTS QPTKQPISQP   240
INQPNNIMGD KRGLKGAETM SPAPLFVEVD ILKDSLDSNL EVLYQVSVNA IMFVRVARNM   300
ASNIIIKSVK VGEDILYLND RRLDLILEFT VTSQQGFHMR IYNNDDRTEN GVIGFLCSFI   360
VADHIPKWYN PPNSRR                                                   376

SEQ ID NO: 3            moltype = DNA  length = 531
FEATURE                 Location/Qualifiers
source                  1..531
                        mol_type = other DNA
                        organism = Babesia microti
SEQUENCE: 3
tgtgatgata ttggtagggc taatcataac cccaatatac ataactatcc cgcatttta    60
gaaccgatag acatcgacat aaagtccaca ccagtaccga aggatgttga gtttgacaac   120
ggtgttttta agttagctgg tagtcgcaag acggaattga aactcagacc aaaagttggg   180
ggcaagtact tggaggtctc tcctcatgtt gccgtcgttc aagtttccgt ttccgtttcc   240
gatggaataa taaacgtcta cgaagatgac taccacaaaa ttactgtgaa gcaattcgac   300
atggatggga atatcattat taaacaaagg gaaggtgcaa tttcggctca tccatttgca   360
caattggcat tctctgttgc atcatctgca aacaatgtta ttttagagga aaatgaaatc   420
ttaaagaaga atattctcga agataacaaa gataatagtc aatcagacgg ggaaattgct   480
tctgaacaag aaaaaactag cactttatca ttccatcat cgccatcatc a            531

SEQ ID NO: 4            moltype = AA  length = 177
FEATURE                 Location/Qualifiers
source                  1..177
                        mol_type = protein
                        organism = Babesia microti
```

-continued

```
SEQUENCE: 4
CDDIGRANHN PNIHNYPAFL EPIDIDIKST PVPKDVEFDN GVFKLAGSRK TELKLRPKVG  60
GKYLEVSPHV AVVQVSVSVS DGIINVYEDD YHKITVKQFD MDGNIIIKQR EGAISAHPFA  120
QLAFSVASSA NNVILEENEI LKKNILEDNK DNSQSDGEIA SEQEKTSTLS FPSSPSS     177

SEQ ID NO: 5            moltype = DNA  length = 756
FEATURE                 Location/Qualifiers
source                  1..756
                        mol_type = other DNA
                        organism = Babesia microti
SEQUENCE: 5
ccatcaaatg gcctctatga atctaacctt ttttacacgg aaggttatgg caaatatttg  60
actagtccga ctaagataaa gacaattgaa tttggaggtt ataaattcga gtttgatgat  120
gatacattgc ctgtaacatc tataacaaaa atcgatgtaa taacatatga tgataaaccg  180
attttatttg aatttatttc agataaggat cgtccataca gaagatttta ctactatact  240
ttggatagta aaactaataa attatataat tatgtcactg cagaaactgg atataatgtt  300
gaggattcga gtggtctaaa atactacact gaattaagta aatcgggaat aaatgatgtt  360
ttacaagatt tggataaaaa cattgatgaa agtaatatcg agcatttgaa gacatcatat  420
gtaacaaaag gattaaatat tgcgattgaa gtttattcaa acagagtcgt tgaacaaatt  480
aaatcgataa aggtagttac tccagttgaa ttattcgatt ataaaactga agttccaatt  540
gagtctgtag atcatgaatc gcgtgataat tcattggccg aagtagagga ggatggaaaa  600
gctgtacaag ttgggactca acctgtgtat gaggtaaatg atggtgctca taacccatct  660
gcacaagtgt tatcacagaa taatattatt gagaccttgg atgataaatc taaagttact  720
catttgagaa atgctggcag tgagaaaatt cgtgtt                            756

SEQ ID NO: 6            moltype = AA  length = 252
FEATURE                 Location/Qualifiers
source                  1..252
                        mol_type = protein
                        organism = Babesia microti
SEQUENCE: 6
PSNGLYESNL FYTEGYGKYL TSPTKIKTIE FGGYKFEFDD DTLPVTSITK IDVITYDDKP  60
ILFEFISDKD RPYRRFYYYT LDSKTNKLYN YVTAETGYNV EDSSGLKYYT ELSKSGINDV  120
LQDLDKNIDE SNIEHLKTSY VTKGLNIAIE VYSNRVVEQI KSIKVVTPVE LFDYKTEVPI  180
ESVDHESRDN SLAEVEEDGK AVQVGTQPVY EVNDGAHNPS AQVLSQNNII ETLDDKSKVT  240
HLRNAGSEKI RV                                                      252

SEQ ID NO: 7            moltype = DNA  length = 2841
FEATURE                 Location/Qualifiers
source                  1..2841
                        mol_type = genomic DNA
                        organism = Babesia microti
SEQUENCE: 7
atggtacaca taactaataa aaagatcctc tacataactg caggttcctt tcttttgcta  60
acgacaataa ttttgccatt agcattgata tttccaaaat catctgtaga gtttgttgac  120
ctgcatttat ccgacaatct tcccaaatat tacagcattc aatatacgca aaatagactt  180
caaattaaaa taaatgatga attttctgat aaatttttca ttaagaaagt cttcatgcct  240
aatgaaacga ccgtttttga aattgaaggg aataaatcag ccgttataaa catcaaattt  300
tctggtgata cattcaaatt caatatcctt gatattgaaa agtctacata tacagaatac  360
gatggtattc acatagaaga tgacaattcg tggatcttat atgccattgg attggtcaag  420
ccatttcctc gtgttgaagt tgattattct attgaaaagg tgaacttccg tatctcagaa  480
aaaatgcccc ttaattacat cctcgtaaat tcaattgacg gtgtatattt tgctttagat  540
ggcattatta atctgtcaag cattggaaac gtatacgtag acgaagattt tgtaccattg  600
cctaagggat ccaagttgag aacagttcat ataaatactc agtacatctt gagtgtaatt  660
gacttatacg atggatatta taagatttct tactccaagt tcgttgatcc tgttaaacta  720
ccagtctcaa tctcaagtgt catttccatt agttctgcct ttaaaacagt cagcttaaaa  780
gagttcttca tgcaatatat atataccata atcgattata aaaatatgta tcgctctgaa  840
ttggtgaaat tctggctgga cctttccagt aaaaatgtct ttgctgatat tgatgttttg  900
atgttaaatg gatacatata tatgtatacc ccaaatccca actacaacat tggagcttta  960
acagtcgggg agacggtgtt gtatcaaggc gatccaattt cacgctctag ggccgtatta  1020
ctcaagaata tttccggcga atggtatgct atggtggtcg atgtataccc tcattttgat  1080
atgatcaatc gcggcctttc gcccctgaaa aagatgaatg gtatggattt atttctagag  1140
aatttgaaca gagtgtattt aaaaaaattt aaccataaat tacctgatgc tacaagcaaa  1200
caattaacaa cactctctga tggtatcaaa gaactagagt taattttcgg aagctttgac  1260
gagtccccca tcgatgttta caacatacgt atattgacag attccgcttt aacccaaaag  1320
tacttgaagg agtatgcgag cattattatg gacattgacc ttgatgtgga tgttttgccg  1380
cccgaagtag aatgtatcac gggggattta ctgctgttga caactttgga tctgaaaaaa  1440
ttagatttca aaattattgg gcgtgtaaaa tggggagaac atatcattga acccaaagcc  1500
acgactctcc tgcggtcaat tcttatattg cacgttaata ccggctatgt gttttgtgtc  1560
atcgatgttg acatctacgc taaaatcaac gtccctggca tctatcgagc gcctgataaa  1620
ctccccaaat ggatcaaacc cttgccgata atccctatta ttggattgaa agagcctctt  1680
tcttggggca tatcaactat ccgctatttt gctaagcaga ctttcatcaa aaacaaatct  1740
ctcactaatc ctggcgtgga caatccgaac ttatctgaag gagtcgttcc atccgatgaa  1800
catatttctt cgcaatccca aatccaactt ttgagcccac tagcaacacc atttcaagtg  1860
atacatctca accaatcaac caaccaacca atcaaccaac caaccaatca accagtcaac  1920
caaccaacca accaatcaac caaccaacca accaatcaac caaccaacca accaaccaac  1980
caatcaacca accaaccaac caatcaacca aacaaccaac caaccaacca atcaaccaaa  2040
caaccaacca accaaccagt caaccaatca accaaccaac caatcaacca atcaaccaaa  2100
caaccaaaca accaaccaat caaccaatca accaaacaac caaccaacca accagtcaac  2160
```

```
caaccaaaca accagtcaac caaccaacca accaatcaac caatcaacca aacaaccaat  2220
caaccaaaca accaaccaac cagtcaacca accaatcaac cagtcaacca accaatcaac  2280
cagtcaacca accaaacaac caatcagtca accaaccaac caatcaacca atcaaccaaa  2340
caaccaacca aacaaccaac caaccaacca aacaaccaaa caaccaacca atcaaccagt  2400
caaccaacca aacaaccaat cagtcaacca atcaaccaac caaacaatat aatgggagat  2460
aagcggggcc tcaaaggcgc tgaaaccatg agtcctgcgc ccctattcgt tgaagttgac  2520
atcctgaaag attctttgga tagtaactta gaagtattat atcaagttag tgttaatgct  2580
attatgtttg tccgcgtcgc tagaaacatg gcctcaaaca tcataattaa aagtgtaaag  2640
gttggagaag atattttgta tttaaatgat cgaagacttg acctaattct tgaatttaca  2700
gttacttctc aacagggttt ccatatgagg atctacaata atgatgatcg tacggagaat  2760
ggtgttatcg gctttctttg ttctttcata gttgcagatc atattcctaa gtggtacaat  2820
ccacctaact cacgccgtta a                                            2841

SEQ ID NO: 8           moltype = AA  length = 946
FEATURE                Location/Qualifiers
source                 1..946
                       mol_type = protein
                       organism = Babesia microti
SEQUENCE: 8
MVHITNKKIL YITAGSFLLL TTIILPLALI FPKSSVEFVD LHLSDNLPKY YSIQYTQNRL   60
QIKINDEFSD KFFIKKVFMP NETTVFEIEG NKSAVINIKF SGDTFKFNIL DIEKSTYTEY  120
DGIHIEDDNS WILYAIGLVK PFPRVEVDYS IEKVNFRISE KMPLNYILVN SIDGVYFALD  180
GIIINLSSIGN VYVDEDFVPL PKGSKLRTVH INTQYILSVI DLYDGYYKIS YSKFVDPVKL  240
PVSISSVISI SSAFKTVSLK EFFMQYIYTI IDYKNMYRSE LVKFWLDLSS KNVFADIDVL  300
MLNGYIYMYT PNPNYNIGAL TVGETVLYQG DPISRSRAVL LKNISGEWYA MVVDVYPHFD  360
MINRGLSPLK KMNGMDLFLE NLNRVYLKKF NHKLPDATSK QLTTLSDGIK ELELIFGSFD  420
ESPIDVYNIR ILTDSALTQK YLKEYASIIM DIDLDVDVLP PEVECITGDL LLLTTLDLKK  480
LDFKIIGRVK WGEHIIEPKA TTLLRSILIL HVNTGYVFCV IDVDIYAKIN VPGIYRAPDK  540
LPKWIKPLPI IPIIGLKEPL SWGISTIRYF AKQTFIKNKS LTNPGVDNPN LSEGVVPSDE  600
HISSQSQIQL LSPLATPFQV IHLNQSTNQP INQPTNQPVN QPTNQSTNQP TNQPTNQPTN  660
QSTNQPTNQP NNQPTNQSTK QPTNQPVNQS TNQPINQSTK QPNNQPINQS TKQPTNQPVN  720
QPNNQSTNQP TNQPINQTTN QPNNQPTSQP TNQPVNQPIN QSTNQTTNQS TNQPINQSTK  780
QPTKQPTNQP NNQTTNQSTS QPTKQPISQP INQPNNIMGD KRGLKGAETM SPAPLFVEVD  840
ILKDSLDSNL EVLYQVSVNA IMFVRVARNM ASNIIIKSVK VGEDILYLND RRLDLILEFT  900
VTSQQGFHMR IYNNDDRTEN GVIGFLCSFI VADHIPKWYN PPNSRR                946

SEQ ID NO: 9           moltype = DNA  length = 816
FEATURE                Location/Qualifiers
source                 1..816
                       mol_type = genomic DNA
                       organism = Babesia microti
SEQUENCE: 9
atgacagtaa caactatcgc attgactgtt tcaatcgtat catatataca tggttctcca   60
tcaaatggcc tctatgaatc taacctttt tacacggaag gttatggcaa atatttgact  120
agtccgacta agataaagac aattgaattt ggaggttata aattcgagtt tgatgatgat  180
acattgcctg taacatctat aacaaaaatc gatgtaataa catatgatga taaaccgatt  240
ttatttgaat ttatttcaga taaggatcgt ccatacagaa ttttacta ctatactttg   300
gatagtaaaa ctaataaatt ataataattat gtcactgcag aaactggata taatgttgag  360
gattcgagtg gtctaaaata ctacactgaa ttaagtaaat cgggaataaa tgatgtttta  420
caagatttgg ataaaaacat tgatgaaagt aatatcgagc atttgaagac atcatatgta  480
acaaaaggat taaatattgc gattgaagtt tattcaaaca gagtcgttga acaaattaaa  540
tcgataaagg tagttactcc agttgaatta ttcgattata aaactgaagt tccaattgag  600
tctgtagatc atgaatcgcg tgataattca ttggccgaag tagaggagga tggaaaagct  660
gtacaagttg ggactcaacc tgtgtatgag gtaaatgatg gtgctcataa cccatctgca  720
caagtgttat cacagaataa tattattgag accttggatg ataaatctaa agttactcat  780
ttgagaaatg ctggcagtga gaaaattcgt gtttaa                            816

SEQ ID NO: 10          moltype = AA  length = 271
FEATURE                Location/Qualifiers
source                 1..271
                       mol_type = protein
                       organism = Babesia microti
SEQUENCE: 10
MTVTTIALTV SIVSYIHGSP SNGLYESNLF YTEGYGKYLT SPTKIKTIEF GGYKFEFDDD   60
TLPVTSITKI DVITYDDKPI LFEFISDKDR PYRRFYYYTL DSKTNKLYNY VTAETGYNVE  120
DSSGLKYYTE LSKSGINDVL QDLDKNIDES NIEHLKTSYV TKGLNIAIEV YSNRVVEQIK  180
SIKVVTPVEL FDYKTEVPIE SVDHESRDNS LAEVEEDGKA VQVGTQPVYE VNDGAHNPSA  240
QVLSQNNIIE TLDDKSKVTH LRNAGSEKIR V                                 271
```

ENHANCED CHEMILUMINESCENT ENZYME-LINKED IMMUNOSORBENT ASSAY FOR DETECTION OF ANTIBODIES AGAINST *BABESIA microti*

CROSS REFERENCE TO RELATED APPLICATIONS

This application is a continuation of U.S. application Ser. No. 16/761,034, filed May 1, 2020, issued as U.S. Pat. No. 11,639,930 on May 2, 2023, which is the U.S. National Stage of International Application No. PCT/US2018/058723, filed Nov. 1, 2018, published in English under PCT Article 21(2), which claims priority to U.S. Provisional Application No. 62/580,588, filed Nov. 2, 2017. The above-listed applications are herein incorporated by reference in their entirety.

FIELD

This disclosure concerns identification of immunodominant *Babesia microti* antigens and their use in immunological detection assays.

INCORPORATION OF ELECTRONIC SEQUENCE LISTING

The electronic sequence listing, submitted herewith as an XML file named 9531-99608-04.xml (17,664 bytes), created on Mar. 17, 2023, is herein incorporated by reference in its entirety.

BACKGROUND

*Babesia microti*, an intraerythrocytic protozoan parasite belonging to phylum Apicomplexan, is the causative agent of human babesiosis. *Ixodes scapularis*, or the deer tick, is the primary vector that transmits this parasite to humans and its natural host, white-footed mice, during a blood meal. Babesiosis can also be transmitted by transfusion of blood and blood products collected from an infected donor (Mintz et al., *Transfusion* 31:365, 1991). Human infection with *Babesia microti* is reported in Europe, Asia and Australia, but the highest prevalence of both tick- and transfusion-transmitted infections occurs in the United States with foci in the Northeast and upper Midwest. Since the first report of babesiosis in the United States on Nantucket in 1969, the geographic range and incidence have been increasing. The Centers for Disease Control and Prevention (CDC) now classifies human babesiosis as an emerging and nationally notifiable disease. Most healthy adults infected by *Babesia* are asymptomatic; however, the disease can be fatal in the elderly, immunocompromised patients regardless of age and asplenic individuals (Vannier et al., *Infect Dis Clin North Am* 29:357, 2015; Homer et al., *Clin Microbiol Rev* 13:451, 2000). Asymptomatic individuals infected with *Babesia* represent a potential public health risk as there is currently no licensed donor screening assay for *Babesia*. Transfusion-transmitted babesiosis (TTB) is a major blood safety concern in United States; about cases of TTB are reported annually with mortality rate as high as 20% (Kleinman and Stassinopoulos, *Transfusion* 55:2983, 2015). Since 1979, when the first U.S. case of TTB was reported, more than 250 cases of TTB and 28 associated deaths have been documented in 22 states, although the actual numbers of cases are thought to be much higher (Herwaldt et al., *Ann Intern Med* 155:509, 2011; Kleinman and Stassinopoulos, *Transfusion* 55:2983, 2015).

The full genome sequence for *B. microti* became available in 2012 (Cornillot, E et al., *Nucleic Acids Res* 40:9102, 2012). However, there is a scarcity of well-characterized, immunodominant *B. microti* antigens for applications in diagnostic assays and vaccine development. Among the currently available antibody-based assays, immunofluorescence assay (IFA) is the most sensitive and specific while the enzyme immunoassay (EIA)-based tests, which require antigenic recombinant proteins or synthetic peptides, have been less successful.

SUMMARY

Disclosed herein is the identification of three highly immunodominant *B. microti* antigens, referred to as *B. microti* serine rich antigen (BmSERA), *B. microti* maltese cross form related protein (BmMCFRP) and *B. microti* piroplasma β-strand (BmPiβS). These antigens were identified by genome-wide screening of a *B. microti* cDNA phage display library against a pool of human sera from babesiosis patients. Use of the immunodominant antigens in immunological assays for the detection of *B. microti*-specific antibodies is further disclosed.

Provided herein are methods for detecting antibodies specific for *B. microti* in a biological sample. In some embodiments, the methods include providing at least one immunodominant *B. microti* antigenic polypeptide immobilized on a solid support; contacting the solid support with the biological sample under conditions sufficient to allow binding of any *B. microti*-specific antibodies present in the biological sample to the at least one *B. microti* antigenic polypeptide, thereby forming antigen-antibody complexes; and detecting the antigen-antibody complexes. In some examples, the at least one antigenic polypeptide is selected from a polypeptide comprising an amino acid sequence at least 90% identical to SEQ ID NO: 2 (BmSERA), a polypeptide comprising an amino acid sequence at least 90% identical to SEQ ID NO: 4 (BmMCFRP) and a polypeptide comprising an amino acid sequence at least 90% identical to SEQ ID NO: 6 (BmPiβS). In specific non-limiting examples, the at least one antigenic polypeptide comprises BmSERA, BmMCFRP and BmPiβS.

Also provided herein are kits, such as for the detection of *B. microti*-specific antibodies in a biological sample. In some embodiments, the kits include at least one immunodominant *B. microti* antigenic polypeptide. In some examples, the at least one antigenic polypeptide is selected from a polypeptide comprising an amino acid sequence at least 90% identical to SEQ ID NO: 2 (BmSERA), a polypeptide comprising an amino acid sequence at least 90% identical to SEQ ID NO: 4 (BmMCFRP) and a polypeptide comprising an amino acid sequence at least 90% identical to SEQ ID NO: 6 (BmPiβS).

Further provided are fusion proteins and compositions that include a disclosed immunodominant *B. microti* antigenic polypeptide.

Isolated nucleic acid molecules and vectors encoding an immunodominant *B. microti* antigenic polypeptide are also provided herein.

The foregoing and other objects, features, and advantages of the invention will become more apparent from the following detailed description, which proceeds with reference to the accompanying figures.

SEQUENCE LISTING

Figure 1:
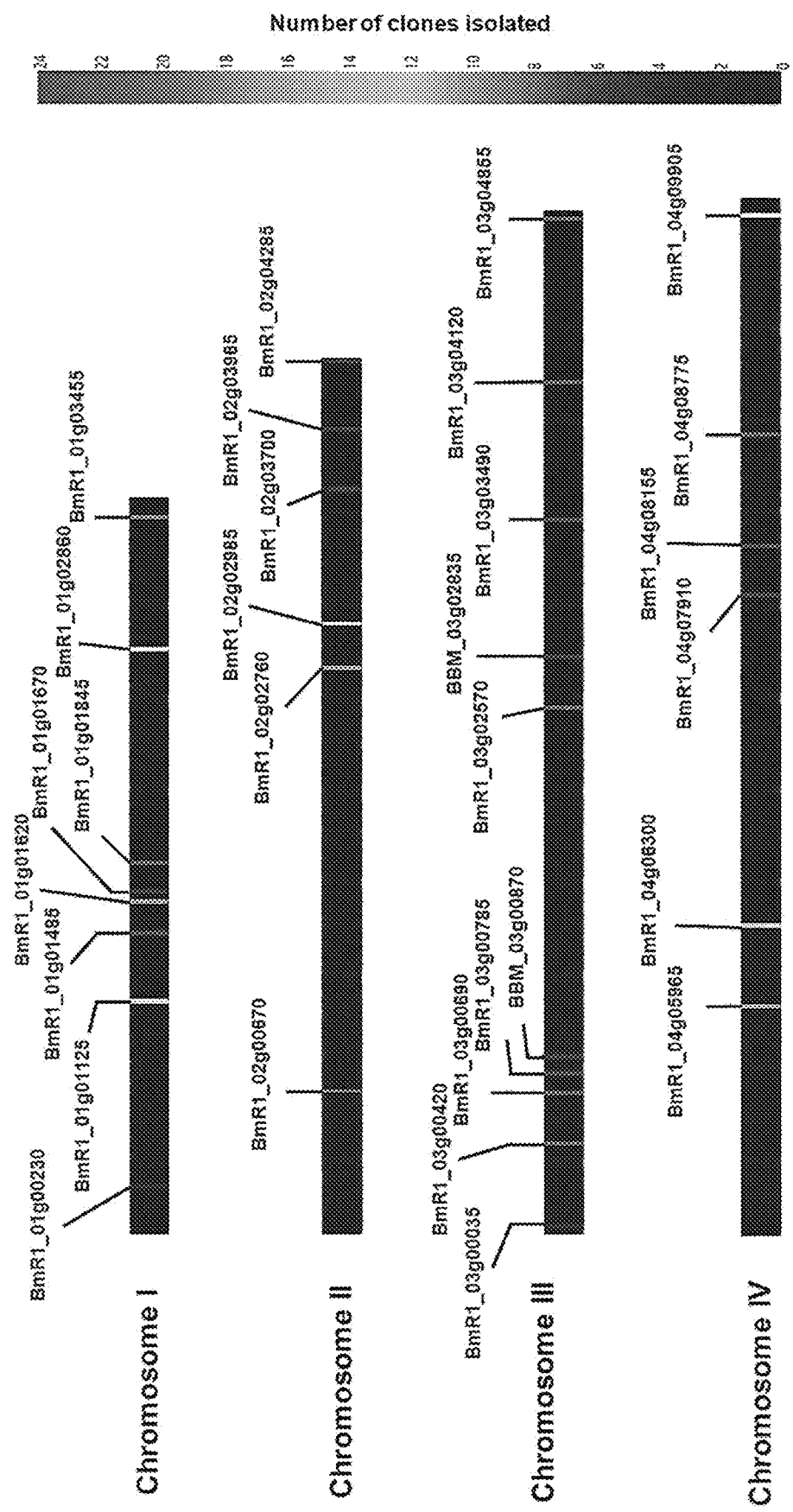
FIG. 1 is a schematic showing genome distribution of *B. microti* immunodominant antigens. The scale bar denotes the number of phage clones isolated for a specified gene following immunoscreening.

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the cDNA sequence encoding an antigenic *B. microti* serine rich antigen (BmSERA) polypeptide.

SEQ ID NO: 2 is the amino acid sequence of an antigenic BmSERA polypeptide.

SEQ ID NO: 3 is the cDNA sequence encoding an antigenic *B. microti* maltese cross form related protein (BmMCFRP) polypeptide.

SEQ ID NO: 4 is the amino acid sequence of an antigenic BmMCFRP polypeptide.

SEQ ID NO: 5 is the cDNA sequence encoding an antigenic *B. microti* piroplasma strand (BmPiβS) polypeptide.

SEQ ID NO: 6 is the amino acid sequence of an antigenic BmPiβS polypeptide.

SEQ ID NO: 7 is the nucleotide sequence encoding the full-length BmSERA protein, deposited under GenBank Accession No. XM_012794769.

SEQ ID NO: 8 is the amino acid sequence of the full-length BmSERA protein, deposited under GenBank Accession No. XP_012650223.

SEQ ID NO: 9 is the nucleotide sequence encoding the full-length BmPiβS protein, deposited under GenBank Accession No. XM_012794124.

SEQ ID NO: 10 is the amino acid sequence of the full-length BmPiβS protein, deposited under GenBank Accession No. XP_012649578.

DETAILED DESCRIPTION

I. Abbreviations

BmELISA *Babesia microti* enzyme-linked immunosorbent assay
BmMCFRP *B. microti* maltese cross form related protein
BmPiβS *B. microti* piroplasma β-strand
BmSERA *B. microti* serine rich antigen
BSA bovine serum albumin
cDNA complementary DNA
DAPI 4',6-diamidino-2-phenylindole
EGF epidermal growth factor
EIA enzyme immunoassay
ECL-ELISA enhanced chemiluminescence enzyme-linked immunosorbent assay
ELISA enzyme-linked immunosorbent assays
HRP horseradish peroxidase
IB inclusion body
IFA immunofluorescence assay
IPTG isopropyl β-D-1-thiogalactopyranoside
RBC red blood cell
RLU relative light units
RT room temperature
SNP single nucleotide polymorphism
TM transmembrane
TTB transfusion-transmitted babesiosis

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

An antibody is a protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. Similarly, an "antigenic" polypeptide is a polypeptide capable of inducing an immune response, such as the production of antibodies.

Antigen-specific: As used herein, an "antigen-specific" antibody is an antibody that was elicited (produced and/or activated) in response to a particular antigen. An "antigen-specific" antibody is capable of binding to the antigen, typically with high affinity.

*Babesia microti*: A protozoan parasite that infects erythrocytes and causes a benign to fatal disease called babesiosis. Transmission of *B. microti* between humans is most often attributable to a tick vector, but can also occur by transfusion of blood and blood products obtained from infected blood donors.

*Babesia microti* Serine Rich Antigen (BmSERA): A 946 amino acid protein with homology to serine-repeat antigen 4 (SERA). Bioinformatics analysis disclosed herein confirmed the localization of this protein as secreted/cell surface. A sequence homology search identified a homolog in the Munich strain of *B. microti* where it reportedly has similar antigenic properties. BmSERA has 16 repeats of the sequence TNQP (residues 57-60 of SEQ ID NO: 2); the significance of this repeat sequence is not yet known. Similar four amino acid repeat sequences have been shown in several of the *Plasmodium falciparum* surface proteins (for example, circumsporozoite protein and merozoite surface protein). The predicted surface localization and the antigenic property of this protein confirm its immunogenicity and establish the molecule as having diagnostic potential. BmSERA mRNA and protein sequences are set forth herein as SEQ ID NOs: 7 and 8, respectively (see also GenBank Accession Nos. XM_012794769 and XP_012650223). A cDNA sequence encoding an antigenic BmSERA polypeptide is set forth herein as SEQ ID NO: 1. The amino acid sequence of the antigenic BmSERA polypeptide is set forth herein as SEQ ID NO: 2.

*Babesia microti* Maltese Cross Form Related Protein (BmMCFRP): A hypothetical protein of 177 amino acids with homology to maltese cross form related protein (GenBank Accession No. AB079857.1). This protein is thought to be involved in cytoskeleton remodeling, which provides evidence for its localization on the cell surface. A cDNA sequence encoding an antigenic BmMCFRP polypeptide is set forth herein as SEQ ID NO: 3. The amino acid sequence of the antigenic BmMCFRP polypeptide is set forth herein as SEQ ID NO: 4.

*Babesia microti* Piroplasma β-Strand domain (BmPiβS): A 271 amino acid protein belonging to the BMN2 family of proteins. The presence of an amino terminal signal sequence makes it a secreted protein. The BmPiβS protein may play an important role in host-parasite dynamics. It is believed to be expressed on the cell-surface at the interface with the host immune system. BmPiβS mRNA and protein sequences are set forth herein as SEQ ID NOs: 9 and 10, respectively (see also GenBank Accession Nos. XM_012794124 and XP_012649578). A cDNA sequence encoding an antigenic BmPiβS polypeptide is set forth herein as SEQ ID NO: 5. The amino acid sequence of the antigenic BmPiβS polypeptide is set forth herein as SEQ ID NO: 6.

Babesiosis: A malaria-like parasitic disease caused by infection with *Babesia*, a genus of Apicomplexa. Babesiosis typically occurs in the Northeastern and Midwestern United States and parts of Europe. Common symptoms of babesiosis include fever, hemolytic anemia, malaise and fatigue. Humans usually develop signs of illness 1 to 4 weeks after being bitten by a tick vector or 1 to 9 weeks after transfusion with contaminated RBCs.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) and bronchoalveolar lavage (BAL) fluid.

Conjugated: Refers to two molecules that are bonded together, for example by covalent bonds.

Contacting: Placement in direct physical association; includes both in solid and liquid form. In some examples, "contacting" refers to incubating a molecule (such as an antigen) with a biological sample. As used herein, "contacting" is used interchangeably with "exposed."

Control: A reference standard, for example a positive control or negative control. A positive control is known to provide a positive test result. A negative control is known to provide a negative test result. However, the reference standard can be a theoretical or computed result, for example a result obtained in a population.

Fluorescent protein: A protein that emits light of a certain wavelength when exposed to a particular wavelength of light. Fluorescent proteins include, but are not limited to, green fluorescent proteins, blue fluorescent proteins, cyan fluorescent proteins, yellow fluorescent proteins, orange fluorescent proteins, red fluorescent proteins and modified versions thereof.

Fluorophore: A chemical compound, which when excited by exposure to a particular wavelength of light, emits light (i.e., fluoresces), for example at a different wavelength.

Examples of fluorophores that may be used in the compositions and methods disclosed herein are provided in U.S. Pat. No. 5,866,366 to Nazarenko et al.: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; R-phycoerythrin; o-phthaldialdehyde; pyrene and derivatives such as pyrene, pyrene butyrate and succinimidyl 1-pyrene butyrate; Reactive Red 4 (Cibacron®, Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine;

tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999).

Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art may also be used.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heterologous: A heterologous protein or polypeptide refers to a protein or polypeptide derived from a different source or species.

Isolated: An "isolated" biological component (such as a nucleic acid molecule, protein, antibody or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins (including antibodies) that have been "isolated" include those purified by standard purification methods. The term also embraces nucleic acid molecules, proteins and antibodies prepared by recombinant expression in a host cell as well as chemically synthesized nucleic acid molecules, proteins and antibodies.

Label: A compound or composition conjugated directly or indirectly to another molecule, such as an antibody, protein or microparticle/microsphere, to facilitate detection of that molecule. As used herein, "label" is used interchangeably with "detectable label." Specific, non-limiting examples of labels include fluorescent tags, enzymes, and radioactive isotopes. "Labeling" refers to the act of linking a label to a molecule of interest, for example linking to the molecule of interest a component that subsequently binds a detectable label or linking a detectable label itself to the molecule of interest, or both. Various methods of labeling polypeptides and other molecules are known in the art and may be used. Examples of detectable labels for polypeptides include, but are not limited to, the following: radioisotopes or radionucleotides (such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I), fluorescent labels (such as fluorescent proteins, fluorophores, fluorescein isothiocyanate (FITC), rhodamine, lanthanide phosphors), enzymatic labels (such as horseradish peroxidase, beta-galactosidase, luciferase, alkaline phosphatase), chemiluminescent markers, chromophores (such as horseradish peroxidase or alkaline phosphatase), biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

A conservative substitution in a polypeptide is substitution of one amino acid residue in a protein sequence for a different amino acid residue having similar biochemical properties. Typically, conservative substitutions have little to no impact on the activity of a resulting polypeptide. For example, a *B. microti* protein including one or more conservative substitutions (for example no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Purified: The term purified does not require absolute purity; rather, it is intended as a relative term. Thus, for example, a purified protein/polypeptide preparation is one in which the polypeptide or protein is more enriched than the polypeptide or protein is in its natural environment within a cell. In one embodiment, a preparation is purified such that the protein or polypeptide represents at least 50% of the total polypeptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Secondary antibody: An antibody that specifically recognizes the Fc region of a particular isotype of antibody (for example specifically recognizes human IgG or human IgM). Secondary antibodies for use with the methods and kits disclosed herein include, but are not limited to, anti-human IgG and anti-human IgM. In some embodiments herein, the secondary antibody is conjugated to a detectable label, such as a fluorophore, enzyme or radioisotope, to facilitate detection of immune complexes to which the secondary antibody is bound.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Serum: The fluid portion of the blood that separates out from clotted blood. Serum contains many proteins, including antibodies, but does not contain clotting factors.

Solid support: Any inert material having a rigid or semi-rigid surface. In the context of the present disclosure, the solid support is capable of binding directly or indirectly to a polypeptide or an antibody (such as a secondary antibody). The solid support can have any shape, form or size (for example, plate, sheet, tube, stick or particle). In some embodiments herein, the solid support is a multi-well plate (also referred to as a microtiter or microwell plate), membrane, glass, metal, bead, microsphere, test tube, test stick, test strip, porous matrix or resin. In some examples, the solid support includes polystyrene, polyethylene or polypropylene.

Subject: Living multi-cellular vertebrate organisms, a category that includes human and non-human mammals.

Synthetic: Produced by artificial means in a laboratory, for example a synthetic nucleic acid or polypeptide can be chemically synthesized in a laboratory.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

The present disclosure describes the use of a *B. microti* bacteriophage display library to identify immunodominant *B. microti* antigens. The immunodominant antigens were evaluated in immunodetection assays, including an enhanced chemiluminescence enzyme-linked immunosorbent assay (ECL-ELISA), to detect *B. microti*-specific antibodies in serum samples from babesiosis patients. Phage display is a selection technique in which a library of peptide or protein variants is expressed on the outside of a phage virion, while the genetic material encoding each variant resides in the phage genome. Thus, each variant protein sequence is physically linked to the DNA it encodes (Smith, *Science* 228:1315, 1985). The *B. microti* phage display library was constructed from parasite complementary DNA (cDNA) and subjected to affinity selection on a pooled panel of babesiosis patient sera. The *B. microti* cDNA library was cloned into the gene encoding viral surface protein gIIIp such that the *B. microti* antigens were expressed at the N-terminus of gIIIp and displayed on the surface of M13 phage. The M13 phage display system has been extensively validated for the efficient expression and display of protein domains (Smith, *Science* 228:1315, 1985).

The study disclosed herein identified more than 50 immunodominant *B. microti* antigens, the majority of which had no known function. Bioinformatics analyses were performed to characterize the potential biochemical and cellular functions of each antigen. These antigens were ranked based on their reactivity to the pooled babesiosis patient sera and 19 of the top-ranking antigens were tested in ELISA for their potential as diagnostic antigens. After extensive performance testing and validation, the three most immuno-reactive antigens were identified, which are referred to herein as *Babesia microti* SErine Repeat Antigen (BmSERA), *Babesia microti* Maltese Cross Form Related Protein (BmMCFRP) and *Babesia microti* Piroplasma β-Strand domain (BmPiβS). When all three antigens were used in combination, ECL-BmELISA recognized 27/28 (96%) of babesiosis patient sera and 0 of 15 (0%) sera samples from individuals who had no known history of babesiosis. Thus, disclosed herein are immuno-based detection methods that utilize the *B. microti* antigens to identify *B. microti*-specific antibodies in biological samples. Such methods can be used, for example, to diagnose a subject as having a *B. microti* infection or to screen donor blood for exposure to *B. microti*.

IV. Overview of Several Embodiments

Disclosed herein is the identification of three highly immunodominant *B. microti* antigens, referred to as *B. microti* serine rich antigen (BmSERA), *B. microti* maltese cross form related protein (BmMCFRP) and *B. microti* piroplasma β-strand (BmPiβS). These antigens were identified by genome-wide screening of a *B. microti* cDNA phage display library against a pool of human sera from babesiosis patients. Use of the immunodominant antigens in immunological assays for the detection *B. microti*-specific antibodies is further disclosed.

Provided herein is a method for detecting antibodies specific for *B. microti* in a biological sample. In some embodiments, the method includes providing at least one immunodominant *B. microti* antigenic polypeptide immobilized on a solid support; contacting the solid support with the biological sample under conditions sufficient to allow binding of any *B. microti*-specific antibodies present in the biological sample to the at least one *B. microti* antigenic polypeptide, thereby forming antigen-antibody complexes; and detecting the antigen-antibody complexes.

Also provided herein is a method of diagnosing a subject as having a *B. microti* infection. In some embodiments, the method includes providing at least one immunodominant *B. microti* antigenic polypeptide immobilized on a solid support; contacting the solid support with a biological sample obtained from the subject under conditions sufficient to allow binding of any *B. microti*-specific antibodies present in the biological sample to the at least one *B. microti* antigenic polypeptide, thereby forming antigen-antibody complexes; and diagnosing the subject as having a *B. microti* infection by detecting the antigen-antibody complexes.

In some embodiments of the disclosed methods, the at least one antigenic polypeptide is selected from a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA), a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In some examples of the disclosed methods, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP).

In other examples, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In other examples, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In yet other examples, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA), a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In one non-limiting example, the at least one antigenic polypeptide includes a polypeptide comprising an amino acid sequence at least 90% identical to SEQ ID NO: 2, a polypeptide comprising an amino acid sequence at least 90% identical to SEQ ID NO: 4 and a polypeptide comprising an amino acid sequence at least 90% identical to SEQ ID NO: 6.

In another non-limiting example, the at least one antigenic polypeptide includes a polypeptide comprising an amino acid sequence at least 95% identical to SEQ ID NO: 2, a polypeptide comprising an amino acid sequence at least 95% identical to SEQ ID NO: 4 and a polypeptide comprising an amino acid sequence at least 95% identical to SEQ ID NO: 6.

In yet another non-limiting example, the at least one antigenic polypeptide includes a polypeptide comprising the amino acid sequence of SEQ ID NO: 2, a polypeptide comprising the amino acid sequence of SEQ ID NO: 4 and a polypeptide comprising the amino acid sequence of SEQ ID NO: 6.

In some examples, the at least one antigenic polypeptide is selected from a polypeptide comprising the amino acid sequence of SEQ ID NO: 2, a polypeptide comprising the amino acid sequence of SEQ ID NO: 4 and a polypeptide comprising the amino acid sequence of SEQ ID NO: 6.

In some embodiments, detecting the antigen-antibody complexes includes contacting the antigen-antibody complexes with a secondary antibody conjugated to a label; and detecting binding of the secondary antibody to the antigen-antibody complexes. In some examples, the label includes an enzyme and detecting binding of the secondary antibody to the antigen-antibody complexes comprises detecting activity of the enzyme. In specific examples, the enzyme is horseradish peroxidase (HRP). In some examples, the label includes a fluorescent protein and detecting binding of the secondary antibody to the antigen-antibody complexes comprises detecting fluorescence. A suitable label for use in an immunoassay, and a corresponding detection method, can be selected by one skill in the art.

In some examples, the secondary antibody comprises anti-human IgG, anti-human IgM, or both.

In some examples, the biological sample comprises blood or a component thereof, such as serum.

In some embodiments of the method of diagnosing a subject as having a *B. microti* infection, the method further includes treating the *B. microti* infection in the subject. In some examples, treatment of the infection includes administration of one or more of atovaquone, azithromycin, clindamycin and quinine.

Further provided are kits, such as for the detection of *B. microti*-specific antibodies in a biological sample, or the diagnosis of a subject as having a *B. microti* infection. In some embodiments, the kits include at least one immunodominant *B. microti* antigenic polypeptide.

In some embodiments of the disclosed kits, the at least one antigenic polypeptide is selected from a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA), a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In some examples of the disclosed kits, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP).

In other examples, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In other examples, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In yet other examples, the at least one antigenic polypeptide includes a polypeptide comprising an amino acid sequence at least 90%, at least 91%, at least 92%, at least 93%, at least 94%, at least 95%, at least 96%, at least 97%, at least 98% or at least 99% identical to SEQ ID NO: 2 (BmSERA), a polypeptide comprising an amino acid sequence at least 90%, at least 91%, at least 92%, at least 93%, at least 94%, at least 95%, at least 96%, at least 97%, at least 98% or at least 99% identical to SEQ ID NO: 4 (BmMCFRP) and a polypeptide comprising an amino acid sequence at least 90%, at least 91%, at least 92%, at least 93%, at least 94%, at least 95%, at least 96%, at least 97%, at least 98% or at least 99% identical to SEQ ID NO: 6 (BmPiβS).

In one non-limiting example, the at least one antigenic polypeptide includes a polypeptide comprising an amino acid sequence at least 90% identical to SEQ ID NO: 2, a polypeptide comprising an amino acid sequence at least 90% identical to SEQ ID NO: 4 and a polypeptide comprising an amino acid sequence at least 90% identical to SEQ ID NO: 6.

In another non-limiting example, the at least one antigenic polypeptide includes a polypeptide comprising an amino acid sequence at least 95% identical to SEQ ID NO: 2, a polypeptide comprising an amino acid sequence at least 95% identical to SEQ ID NO: 4 and a polypeptide comprising an amino acid sequence at least 95% identical to SEQ ID NO: 6.

In yet another non-limiting example, the at least one antigenic polypeptide includes a polypeptide comprising the amino acid sequence of SEQ ID NO: 2, a polypeptide comprising the amino acid sequence of SEQ ID NO: 4 and a polypeptide comprising the amino acid sequence of SEQ ID NO: 6.

In some examples of the disclosed kits, the at least one antigenic polypeptide is selected from a polypeptide comprising the amino acid sequence of SEQ ID NO: 2, a polypeptide comprising the amino acid sequence of SEQ ID NO: 4 and a polypeptide comprising the amino acid sequence of SEQ ID NO: 6.

In some embodiments of the disclosed kits, the at least one antigenic polypeptide is immobilized on a solid support. In some examples, the solid support comprises a multi-well plate.

Further provided are fusion proteins that include a *Babesia microti* antigenic polypeptide fused to a heterologous peptide. In some embodiments, the heterologous peptide comprises an affinity tag, an epitope tag, a fluorescent protein, an enzyme or a carrier protein. In particular examples, the enzyme is HRP, chloramphenicol acetyl transferase (CAT), β-galactosidase, luciferase or alkaline phosphatase (AP). In particular examples, the affinity tag is chitin binding protein, maltose binding protein, glutathione-S-transferase or poly-His (such as hexa-His). In particular examples, the epitope tag is V5, c-myc, HA or FLAG. In particular examples, the fluorescent tag is GFP or another well-known fluorescent protein. In particular examples, the carrier protein is keyhole limpet hemocyanin (KLH), bovine serum albumin (BSA) or ovalbumin (OVA). In some embodiments, the amino acid sequence of the *B. microti* antigenic polypeptide consists of SEQ ID NO: 2, SEQ ID NO: 4 or SEQ ID NO: 6. In other embodiments, the *B. microti* antigenic polypeptide is at least 80%, at least 85%, at least 90%, at least 91%, at least 92%, at least 93%, at least 94%, at least 95%, at least 96%, at least 97%, at least 98% or at least 99% identical to SEQ ID NO: 4.

Also provided are compositions that include a *Babesia microti* antigenic polypeptide immobilized on a solid support. In some embodiments, the solid support includes a multi-well plate, a membrane, a bead, a microsphere, a test tube, a test stick or a test strip. In some embodiments, the amino acid sequence of the *B. microti* antigenic polypeptide consists of SEQ ID NO: 2, SEQ ID NO: 4 or SEQ ID NO: 6. In other embodiments, the *B. microti* antigenic polypeptide is at least 80%, at least 85%, at least 90%, at least 91%, at least 92%, at least 93%, at least 94%, at least 95%, at least 96%, at least 97%, at least 98% or at least 99% identical to SEQ ID NO: 4.

Further provided are isolated nucleic acid molecules encoding a *Babesia microti* antigenic polypeptide. In some embodiments, the amino acid sequence of the *B. microti* antigenic polypeptide consists of SEQ ID NO: 2, SEQ ID NO: 4 or SEQ ID NO: 6. In some examples, the nucleotide sequence of the isolated nucleic acid molecule consists of SEQ ID NO: 1, SEQ ID NO: 3 or SEQ ID NO: 5. In other examples, the nucleotide sequence of the isolated nucleic acid molecule is at least 80%, at least 85%, at least 90%, at least 91%, at least 92%, at least 93%, at least 94%, at least 95%, at least 96%, at least 97%, at least 98% or at least 99% identical to SEQ ID NO: 3. Vectors that includes an isolated nucleic acid molecule disclosed herein operably linked to a heterologous promoter are also provided.

Also provide is an isolated polypeptide, wherein the amino acid sequence of the polypeptide is at least 80%, at least 85%, at least 90%, at least 91%, at least 92%, at least 93%, at least 94%, at least 95%, at least 96%, at least 97%, at least 98% or at least 99% identical to SEQ ID NO: 4. In some examples, the amino acid sequence of the polypeptide comprises SEQ ID NO: 4. Isolated nucleic acid molecules encoding the isolated polypeptides are further provided.

Further provided is an isolated nucleic acid molecule, comprising a nucleotide sequence at least 80%, at least 85%, at least 90%, at least 91%, at least 92%, at least 93%, at least 94%, at least 95%, at least 96%, at least 97%, at least 98% or at least 99% identical to SEQ ID NO: 3. In some examples, the isolated nucleic acid molecule comprises the nucleotide sequence of SEQ ID NO: 3.

V. Detection of *Babesia microti* Antibodies in Patient Samples and Donor Blood

Serological methods of detecting *B. microti*-specific antibodies in a biological sample, such as a serum or blood sample, are disclosed herein. These methods use the immunodominant *B. microti* antigenic polypeptides disclosed herein. Detection assays based on binding of an antigen to an antibody are well known in the art and include, for example, ELISA, microsphere immunoassay (MIA), immunofluorescence assay (IFA), Western blot, fluorescence activated cell sorting (FACS), radioimmunoassay (RIA) and immunohistochemistry (IHC). As is well known to one of skill in the art, in some cases the detection assay further includes the step of contacting an antigen-antibody complex with a detection reagent, such as a labeled secondary antibody (e.g., an anti-isotype antibody, such as an anti-IgG or anti-IgM antibody), or in the case of a sandwich ELISA, a second antibody that recognizes the same antigen as the first antibody and is labeled for detection. Secondary antibodies can also be conjugated to magnetic beads to allow for magnetic sorting. The *B. microti* antigenic polypeptides disclosed herein can be used with a variety of immuno-based detection assays for the detection of *B. microti*-specific antibodies in patient samples or donor blood, and/or for the diagnosis of *B. microti* infection. Several exemplary immuno-based detection assays are described below.

A. Indirect ELISA

In one embodiment, disclosed herein is an enhanced chemiluminescent ELISA (ECL-ELISA), which is an indirect ELISA. An indirect ELISA is performed by immobilizing antigen, such as an immunodominant *B. microti* antigenic polypeptide, on a solid support, for example the wells of a microtiter plate. A biological sample, such as a diluted serum or blood sample, is added to the immobilized antigen such that any antigen-specific antibodies present in the biological sample will bind to the immobilized antigen. A labelled secondary antibody, such as an anti-IgM or an anti-IgM antibody, is added. The label on the secondary antibody can be, for example, an enzyme or a fluorophore. The detectable label is then measured (activity of the enzyme following addition of an appropriate substrate, or fluorescence) to detect the presence of antigen-specific antibodies that were present in the serum or blood sample.

The ECL-ELISA disclosed herein is described in Example 1. In the ECL-ELISA, one or all three of the disclosed immunodominant *B. microti* antigenic polypeptide(s) is/are immobilized on a multi-well plate. After washing and blocking steps, diluted test serum was added to the wells and incubated. After washing, diluted HRP-conjugated anti-human IgG and IgM antibody was added and incubated. The plates were then washed and SuperSignal™ ELISA Pico Chemiluminescent Substrate (Thermo Fisher Scientific, MA) was added for 5 minutes and relative light units (RLUs) were measured.

B. IgM or IgG Antibody Capture ELISAs

The immune response following a *B. microti* infection includes the production of IgM and IgG antibodies. IgM antibody capture (MAC) or IgG antibody capture (GAC) ELISAs can be used to detect the level of IgM or IgG (respectively) in serum samples of patients suspected of having a *B. microti* infection or to screen donor blood for exposure to *B. microti*. In these assays, anti-human IgM or anti-human IgG serves as a capture antibody and is coated onto an appropriate assay plate, such as a multi-well plate. After blocking of the plate, such as with nonfat dry milk, diluted human sera are reacted with the anti-human IgM or IgG. In the context of the present disclosure, one or more immunodominant *B. microti* antigenic polypeptides are added to the plates. A *B. microti*-specific antibody conjugated directly or indirectly to detectable label (for example, an enzyme or fluorophore) is then reacted with the immobilized antigen. The detectable label is then measured to detect the presence of *B. microti*-specific antibodies that were present in the serum or blood sample. Serial dilutions of positive sera can be evaluated. The maximum dilution that exhibits positive signal is the titer for the serum.

C. Sandwich ELISA

A sandwich ELISA to detect the presence of *B. microti*-specific antibodies can be carried out by coating a microtiter plate with a *B. microti*-specific antibody, blocking the plates to prevent non-specific binding to the plate surface, and adding one or more immunodominant *B. microti* antigenic polypeptides to allow binding of the antigenic polypeptides to the *B. microti*-specific antibody. After washing, samples (such as diluted serum or blood samples) are added to allow binding of any antibodies present in the sample to the immobilized antigenic polypeptides. IgM or IgG antibodies that were present in the sample are then detected using a labelled secondary antibody, such as anti-human IgG or anti-human IgM conjugated to a detectable label (such as an enzyme or fluorophore). The presence of *B. microti*-specific antibodies is detected by measuring the detectable label (for example, by measuring fluorescence, optical density or colorimetric absorbance).

D. Microsphere Immunoassay (MIA)

Microsphere immunoassays are becoming increasingly popular for laboratory diagnosis of many diseases (Earley et al., *Cytometry* 50:239-242, 2002; Kellar et al., *Cytometry* 45:27-36, 2001). The technology involves the detection and analysis of a reaction (such as an antibody or other ligand) attached to microspheres or beads. The detecting instrument is a simplified flow cytometer, and lasers simultaneously identify the microsphere sets and measure the fluorescence associated with the reaction. The speed at which these tests can be performed and the ability to multiplex make this methodology particularly useful.

A MIA can be used to detect the presence of *B. microti*-specific antibodies in a sample. In some embodiments, microsphere beads are coated with a *B. microti*-specific antibody and contacted with immunodominant *B. microti* antigenic polypeptides (as disclosed herein) such that the antigenic polypeptides bind to the microsphere-bound *B. microti*-specific antibodies. The microsphere immune complexes are mixed with a serum sample such that antibodies in the sample that are specifically reactive with an immunodominant *B. microti* antigenic polypeptide bind the antigenic polypeptides bound (indirectly) to the microsphere. The bead-bound immune complexes are allowed to react with fluorescent-dye labeled anti-species antibody (such as PE-labeled anti-human IgM or anti-human IgG), and are measured using a microsphere reader (such as a Luminex instrument). In an alternative embodiment, microsphere beads are coated directly with the immunodominant *B. microti* antigenic polypeptides and antigenic polypeptide-bound microspheres are contacted with the serum samples.

E. Lateral Flow Assay (LFA)

Lateral flow immunoassays are another method by which antigen-specific antibodies can be detected in biological samples. These assays are generally very rapid and enable point of care testing. LFA is performed over a strip, different parts of which are assembled on a plastic backing. These parts are sample application pad, conjugate pad, nitrocellulose membrane and adsorption pad. Nitrocellulose membrane is further divided into test and control lines. Pre-immobilized reagents at different parts of the strip become active upon flow of liquid sample. LFA combines the unique advantages of biorecognition probes and chromatography.

Several designs have been developed for lateral flow assays. Generally, LFAs include a porous support strip (such as a strip of cellulose) with a number of separate regions spaced horizontally along the support. The solid support need not be identical in all regions of a strip. Typically, the first region is a sample pad where a biological fluid is applied to flow laterally through the support to the remaining regions. The second region generally contains a labeling moiety that can be bound to the analyte of interest (such as an antibody or protein) in the sample if present. Downstream of the labeling region is a capture or "test" region where the labeled analyte (for example, antibody or peptide) is retained in the strip. It is in this test region where detection is generally performed. In addition to the test region, the strip may contain a control region either in the same flow path as that of the test region, or in a parallel path on the strip. There may also be a reservoir downstream of the various regions to absorb the sample that has traversed the test strip.

LFAs can be direct assays, forming sandwiches in proportion to the level of analyte present, or may be competition assays where analyte in the sample diminishes the amount of label detected in the detection zone. In direct sandwich assays, for example, the sample may be labeled by colored particles that are coupled to affinity reagents such as secondary antibodies that bind *B. microti*-specific antibodies present in the sample, forming complexes which are then carried to the test region for capture by an additional reagent. The detectable label in the test region will be directly proportional to the level of analyte (such as an antigen-specific antibody) in the sample.

In competitive assays, the labeling region may contain labeled reagents, for example, that are already coupled to the target analyte (e.g. antibody) or an analog thereof, and the analytes in the sample compete with this labeled material for capture by the capture reagent in the test region. In this case, the detectable label in the test region will be inversely proportional to the quantity of analyte in the sample itself.

Simple visual detection is the most common means of reading an LFA, however, there are commercially available lateral flow readers that can quantitate the detectable label in the test region.

The following examples are provided to illustrate certain particular features and/or embodiments. These examples should not be construed to limit the disclosure to the particular features or embodiments described.

EXAMPLES

Example 1: Materials and Methods

This example describes the experimental procedures used for the studies described in Example 2.

*B. microti* Parasites

*B. microti* (Franca) Reichenow Peabody strain (Ruebush, *J Parasitol* 65:430, 1979) was obtained from the American Type Culture Collection (ATCC; Manassas, VA). Female DBA/2NCr mice were injected with *B. microti* parasites and the parasite infected red blood cells (RBCs) were isolated at 15-20% parasitemia.

Construction of *B. microti* cDNA Phage Library

*B. microti* parasites were harvested by lysing the infected RBCs with sarkosyl buffer (10 mM Tris-HCl (pH 7.5), 10 mM EDTA, 10 mM NaCl, 0.5% Sarkosyl). The *B. microti* RNA was prepared using TRIZOL™ reagent (Life Technologies, Grand Island, NY), followed by chloroform extraction and precipitation performed with isopropyl alcohol and ethanol. Complimentary DNA (cDNA) encompassing the entire open reading frames was prepared from the *B. microti* RNA using SMART® cDNA library construction kit (Clontech laboratories, Inc., CA) following the manufacturer's instructions. Briefly, the first strand cDNA was synthesized from the *B. microti* RNA using a modified oligo (dT) primer and SMART IV oligonucleotide primers. The second-strand cDNA was made using Long Distance (LD) PCR conditions. The synthesized double-stranded cDNA (~10 μg) was subjected to controlled fragmentation using sonication (Model FB120; Sonic Dismembrator, Thermo Fisher Scientific, MA) to generate small (50-300 bp) and large (300-1000 bp) cDNA library fragments, which were separated by agarose gel electrophoresis. These cDNA fragments were dephosphorylated and polished to obtain blunt ended fragments to be ligated into Sma I (CCC^GGG) digested M13-derived phage vector. The ligation products were transformed into *Escherichia coli* TG1 cells (Agilent technologies, MD) and selected for recombinants (tet^r) on tetracycline plates. Transformed cells were cultured at 37° C. with shaking at 250 rpm in 100 ml of 2XYT broth containing 5 µg/ml tetracycline for approximately 16 hours. The recombinant lysogenic phages displaying the fusion protein domain were recovered from the supernatant and the phage titer was determined. The cDNA inserts were expressed as $NH_2$-terminal fusion to the gIIIp surface protein of the M13 phage. Both small (50-300 bp) and large fragment (300-1000 bp) *B. microti* libraries yielded $10^6$ independent clones as established by limiting dilution of the transformed bacterial cells. Forty-eight clones were picked from each library and PCR amplified using phage specific primers and sequenced to determine the random distribution and diversity of the *B. microti* genome libraries.

Immunoscreening Via Panning

A pool of seven babesiosis patient sera (anti-*B. microti* IFA titer >1:500) were used for panning of the *B. microti* library. To minimize non-specific reactivity, pooled babesiosis serum was incubated with ultraviolet-killed M13K07 phage-coated petri dishes. For the affinity panning of the phage library, 96-well maxisorp microwell plates (Immulon 4 HBX, Thermo Scientific, Rochester) were coated overnight at 4° C. with 1 µg of goat anti-human IgG Fcγ antibodies in phosphate-buffered saline (PBS), pH 7.4. After three washings with PBST (20 mM PBS (pH 7.4) containing 0.1% Tween 20), 5% bovine serum albumin (BSA fraction V, Sigma-Aldrich) in PBST was added to the wells to block the unoccupied reactive sites. Pre-adsorbed babesiosis patient sera was added to the wells and incubated for 1 hour at room temperature (RT). Wells were washed three times with PBST, and $10^6$ phages from the *B. microti* library were added for 1 hour at RT. Non-adherent phages were removed by 9 washes with PBST followed by 3 washes with PBS. The adherent phages were eluted by the addition of 0.1 N Glycine-HCl (pH 2.2), 100 µl per well for 10 minutes at 37° C. The eluate was immediately neutralized by the addition of 2 M Tris (pH unadjusted). The eluate was simultaneously titrated and amplified for the next round of panning in log phase ($OD_{600\ nm}$~0.8) *E. coli* TG1 cells. For the phage amplification, the phage infected TG1 cells were incubated at 37° C. for 90 minutes without shaking followed by dilution with 10 ml of 2XYT medium containing 5 µg/ml tetracycline and incubated at 37° C., with shaking at 250 rpm for approximately 16 hours. Phage supernatants were collected after centrifugation and one more round of panning was carried out. Phage titration plates were used for picking the colonies and performing PCR amplification and subsequent sequencing to establish the identity of the cloned insert. A total of 960 phage clones were sequenced using phage specific primers. The sequences obtained after Sanger's di-deoxy sequencing were analyzed by Pubmed BLAST to identify the *B. microti* antigen it encodes. Finally, the sequencing reads were aligned to the target sequence in MacVector program.

Phage ELISA to Analyze Affinity-Selected Clones

The reactivity of affinity-selected phage supernatants with babesiosis patient sera was measured by ELISA. The wells of maxisorp microwell plates (Immulon 4 HBX, Thermo Scientific, Rochester) were coated with 50 ng/well of anti-M13 phage antibody (GE Healthcare, Piscataway, NJ) and blocked with 5% skim-milk PBST (0.5% tween-20). Subsequently, phage supernatants of the selected clones were added to each well and incubated for 1 hour at RT. Next, serially diluted sera (in 5% skim-milk PBST) were added and incubated at RT for 1 hour. The bound antibodies were probed with HRP-conjugated goat anti-human IgG antibodies, and the enzymatic activity was revealed by incubating the plates with chromogenic substrate, ABTS (KPL, Inc., Gaithersburg, MD). The genes encoding the domains with high ELISA reactive phage clones were selected for cloning into an *E. coli* expression system.

Recombinant Expression and Purification of *B. microti* Antigens

Expression of recombinant protein was accomplished by amplifying either the full-length gene or a portion thereof encoding a domain of the protein, predicted based on the theoretical antigenicity index using Immune Epitope Database and Analysis Resource (IEDB). The putative signal and transmembrane sequences were identified using SignalP 4.1 Server and TMHMM Server v. 2.0, respectively, and excised in the domain selected for recombinant expression. The PCR-amplified product was cloned into a NotI and Asci (NEB, Ipswich, MA) restriction site in a pET11a vector (MERCK, Germany), which was modified to include a $NH_2$-terminal hexa-histidine tag to facilitate purification. Protein expression was carried out in *E. coli* BL-21 (λDE3) cells with isopropyl β-D-1-thiogalactopyranoside (IPTG) induction. Induced *E. coli* cells were lysed with BUGBUSTER™ Protein Extraction Reagent (EMD Millipore, MA) and the soluble proteins were purified from the supernatant on a HisTrap column (GE Healthcare life sciences, PA). The insoluble proteins were purified using a method as described by Buchner and Rudolph with some modifications (Buchner and Rudolph, *Biotechnology* 9:158, 1991). Essentially, the cells were lysed using a combination of lysozyme and sonication, followed by buffer (50 mM Tris pH 8.0, 20 mM EDTA) washing 4-6 times to obtain pure inclusion bodies (IBs). The insoluble protein in the IBs was denatured in the solubilization buffer (0.1M Tris pH 8.0, 2 mM EDTA, 6M Guanidine HCl) before refolding under controlled redox condition in the renaturation buffer (0.1M Tris pH 8.0, 2 mM EDTA, 0.5 M L-Arginine HCl, 0.9 mM oxidized Glutathione). The refolded protein was dialyzed against a gradient of urea and finally brought into 20 mM Tris pH 8.0 buffer and purified on a HisTrap column. The purified recombinant proteins were quantified using Bradford's reagent (Sigma-Aldrich, MO). The degree of purity of recombinant proteins was determined on SDS-PAGE followed by Coomassie blue staining. Mass spectrometry analysis of the purified recombinant *B. microti* proteins was performed to confirm their identity.

Generation of Antibodies Against Recombinant *B. microti* Antigens

Female Balb/c mice (5-6 weeks old) were purchased from Jackson Laboratories (Bar Harbor, MA). Mice (5 per group) were immunized three times with 50 µg of purified recombinant *B. microti* serine rich antigen (BmSERA), *B. microti* maltese cross form related protein (BmMCFRP) and *B. microti* piroplasma β-strand (BmPiβS) per mouse subcutaneously in Freund's adjuvant (Complete Freund's adjuvant for the primary dose followed by two booster doses in Incomplete Freund's adjuvant) at 3-week intervals. Serum samples were collected two weeks after the third immunization and stored at −20° C. until use.

ELISA

The recombinant *B. microti* antigens were coated overnight (approximately 16 hours) on 96-well maxisorp ELISA plates (Immulon 4 HBX, Thermo Scientific, Rochester) in PBS at 50 ng/well. Plates were washed with PBST (PBS with 0.1% Tween-20) and blocked with blocking buffer (5% skim milk PBS with 0.5% Tween-20) for 2 hours at 37° C. This was followed by washing with PBST. 100-fold diluted serum in blocking buffer was added to the wells and plates were incubated for 1 hour at 37° C., followed by PBST washing and incubating with 1/10,000 diluted HRP-conjugated goat anti-human IgG and IgM antibody for 1 hour at 37° C. Plates were then washed six times with PBST and three times with PBS and then incubated with 50 µl per well of SureBlue Reserve TMB (KPL Inc.) substrate solution for an additional 10 minutes at RT. The reaction was stopped using 50 µl per well of stop solution (Thermo Fisher Scientific, MA). The plates were read at 450 nm using plate reader (SpectraMax384, Molecular devices, CA). The assay cutoff was determined from the mean optical density reading for the *B. microti* negative (n=15) serum samples+2 standard deviations of the mean.

Immunofluorescence Assay (IFA)

For IFA, slides were prepared from *B. microti* infected RBCs and reacted with 128-fold diluted human sera for 1 hour at 37° C. in a humidified chamber. This was followed by three washings with PBS in a coplan jar. The bound antibodies were probed using 2000-fold diluted ALEXA FLOUR™ 488 conjugated goat anti-human IgG antibody in 0.002% Evan's blue solution made in PBS and the slides were again incubated for 1 hour at 37° C. Finally, the slides were washed three times with PBS in a coplan jar in the dark. The slides were mounted with fluoromount slide mounting medium (Electron microscopy sciences, VWR, PA) and sealed with a coverslip. The slides were observed in a fluorescence microscope at 40× resolution under GFP filter.

Enhanced Chemiluminescence *Babesia microti* ELISA (ECL-BmELISA)

The recombinant BmSERA, BmMCFRP and BmPiβS antigens were used to coat the Costar black clear bottom plate (Corning, NY) at 25 ng/well, 50 ng/well and 50 ng/well, respectively, in 1×PBS (10 mM Na2HPO4, 1.8 mM KH2PO4, 2.7 mM KCl, 137 mM NaCl, pH 7.4). For the combination ELISA, the three antigens (BmSERA, BmMCFRP and BmPiβS) were mixed at the concentration of 25 ng/well, 50 ng/well and 50 ng/well, respectively. The plates were incubated overnight (approximately 16 hours) at 4° C. The plates were taken out and incubated at 37° C. for 1 hour, washed 3 times with PBS containing 0.1% Tween-20 (Thermo Fisher Scientific, MA) and blocked for 2 hours at 37° C. with 5% skim milk (Bio-Rad, CA) in 1×PBS with 0.5% Tween-20. Following incubation, the blocking solution was removed by flicking the plates and a 100-fold dilution of the test serum in sample diluent (Blocking buffer with 0.35M NaCl) was added to the wells. The plates were incubated for 1 hour at 37° C. After 3 washings with 1×PBST, 1/10,000 diluted HRP-conjugated goat anti-human IgG and IgM antibody (Jackson Immunoresearch Laboratories, PA) was added and incubated further for 1 hour at 37° C. Finally, the plates were washed 6 times with 1×PBST and 3 times with 1×PBS, before adding SuperSignal™ ELISA Pico Chemiluminescent Substrate (Thermo Fisher Scientific, MA) for 5 minutes at room temperature. The chemiluminescence reading was taken on Victor$^3$V 1420 multi-label counter (Perkin Elmer, MA). The results obtained from the reading are in relative light units (RLUs).

ELISA Assay Cutoff Determination

Cutoff value=mean optical density reading for the *B. microti* negative (n=15) serum samples+2 standard deviations of the mean.

Example 2: ECL-ELISA for the Detection of Antibodies to *B. microti* in Blood Donors This example describes the development of an ELISA to detect *B. microti*-specific antibodies in human serum samples.

Immunoscreening of *B. microti* Antigens

The M13 phage display library displaying the *B. microti* transcriptome was screened with the pooled infected babesiosis patient sera. Following two rounds of panning, a total of 960 clones were isolated and amplified via PCR, before being subjected to nucleotide sequencing. The gene sequences obtained following sequencing were aligned to the target *B. microti* genome, which led to identification of 56 immunodominant *B. microti* antigens. Subsequently, these 56 phage clones displaying distinct *B. microti* antigens were analyzed on a confirmatory phage-ELISA against the pooled infected babesiosis patient sera. A total of 30 high ELISA reactive phage clones displaying specific *B. microti* antigens were selected for antigenic characterization and recombinant expression.

Antigenic Characterization

Availability of whole genome sequence of *B. microti* (Cornillot, et al., *Nucleic Acids Res* 40:9102, 2012) has made in silico analyses of the 30 identified immunodominant antigens feasible. The distribution of the genes encoding these 30 antigens on the chromosomes of *B. microti* is shown in FIG. 1. The genes identified from the phage library based selection appeared to be randomly distributed on all four chromosomes of *B. microti*. This demonstrates that the genes encoding the highly antigenic proteins are not localized to the terminal regions, or more specifically, to the highly variable sub-telomeric region as reported previously (Lodes et al., *Infect Immun* 68:2783, 2000). Most of these antigens have never been characterized and possess an unknown cellular or biological function. Also, none of these antigens share any homology with each other. At the protein level, five antigens, BmR1_03g00690, BmR1_03g04855, BmR1_03g06300, BmR1_03g04120 and BmR1_02g04285, are unique only to *B. microti*. BmR1_02g04285 has high sequence identity to the COOH-terminus region of Maltese cross form related protein. Two of these antigens, BmR1_03g00785 and BmR1_03g04855, are members of the *B. microti* sero-reactive antigen family (bmn) (Lodes et al., *Infect Immun* 68:2783, 2000; Homer et al., *J Clin Microbiol* 38:362, 2000).

Next, the available database (PiroplasmaDB at piroplasmadb.org) was searched to determine the gene copy number of each antigen. Though no estimation of the copy number could be found, the paralogue count for each gene provided a rough estimation for the copy number. Eight of these genes had at least one paralogue. The bmn family members BmR1_03g00785 and BmR1_03g04855 had 9 and 12 paralogues, respectively. BLAST search was performed with 30 high index *B. microti* antigens to identify their orthologs from other apicomplexans. Twenty of these proteins had orthologous proteins in other apicomplexan parasites, whereas 10 of them yielded no similarity. This shows the uniqueness of the proteins identified and their specificity to *B. microti*. The results also suggest that *B. microti* belongs to a distinct lineage of piroplasmida outside the classical *Theileria* and *Babesia* genera in the phylogenetic classification.

Figure 2:
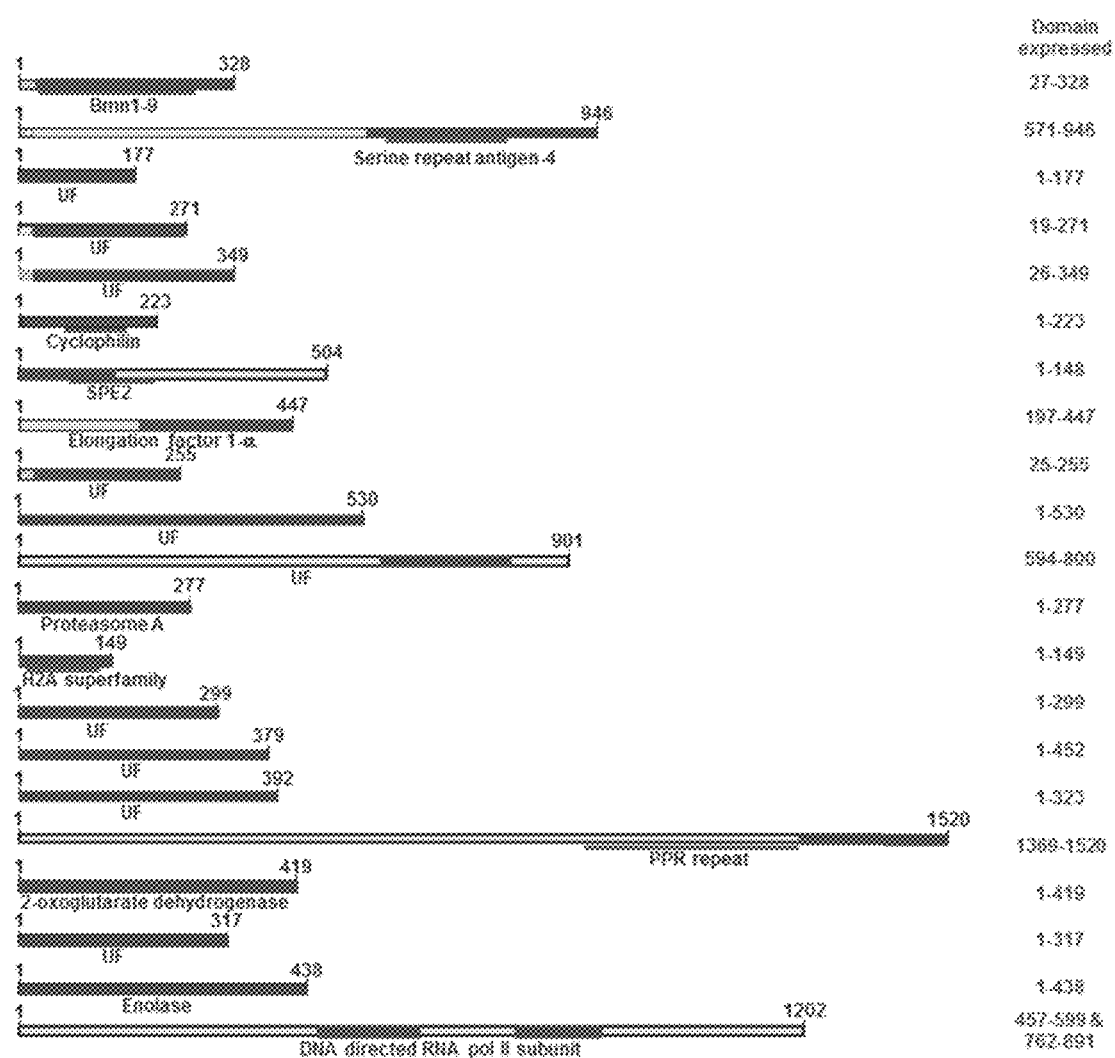
FIG. 2 is a schematic showing the domain architecture of *B. microti* antigens.

The *B. microti* proteins identified using phage display as gIII fusion proteins on M13 phages were cloned as $NH_2$-terminal hexa-histidine tagged in an *E. coli* expression vector for recombinant protein production. Thirty of the most reactive *B. microti* antigens as identified in phage display screening were produced as recombinant proteins in *E. coli*. A map of the protein domain(s) expressed for each identified antigen is shown in FIG. 2.

Bioinformatics Analyses

The four proteins that were identified as antigens in *B. microti* strain RI were subject to in-depth sequence analysis to obtain a better understanding of their evolutionary history and potential functional features. First, their compositional features were analyzed to predict signal, transmembrane (TM) and low complexity regions. This was followed by in-depth sequence analysis using sequence profile searches with the PSI-BLAST program and hidden Markov model searches using the JACKHMMER program. Finally, profile-profile searches with the HHpred program were conducted to detect even more remote relationships. The analysis of the four proteins revealed that all were predicted to contain N-terminal signal peptides consistent with their cell-surface localization as immunogenic antigens.

BmR1_04g08155 is a 946-amino acid protein, which was erroneously annotated as having "homologies with serine-repeat antigen 4." This annotation is unsupported by sequence analysis and arises from improper masking of low complexity sequence. However, this protein has a previously reported homolog in the Munich strain of *B. microti* where it was reported to have antigenic properties consistent with the current study (PMID: 20599995). Remarkably, comparison of BmR1_04g08155 with this protein suggest that it is extremely fast-evolving even between these two strains with a sequence identity just around 43%, which is much higher than the sequence divergence for other available proteins between these two strains (~95-98% identity). This strongly suggests that this protein is evolutionarily responding to host immune responses against it and is consistent with its character as an antigenic secreted/cell surface protein.

BmR1_03g04855 is a member of the so-called "BMN1" class of antigenic proteins, which is shared by different *B. microti* strains and *B. rodhaini*. While some of these related antigens (SA5-1-1, SA26 and SA17) were first identified in *B. rodhaini* in 1988 (PMID: 2893977), several subsequent studies in *B. microti* have misunderstood the evolutionary relationships of these proteins resulting in considerable confusion in their nomenclature in the literature (PMID: 12574273, 10768973, 23291346, 27184823). The sequence analysis disclosed herein shows that the proteins which have been considered BMN1 antigens do not constitute a monophyletic group and should have been included together for construction of phylogenetic trees. Instead the present analysis shows that there are two mostly evolutionarily unrelated groups of BMN1 proteins. The first of these groups includes the previously characterized BMN1-10, N1-10, BMN1-4, BMN1-3B, BMN1-8 and BMN1-11 from the *B. microti* MN1 strain, the IRA protein from the *B. microti* Gray strain and the Br-1 and Br-2 proteins from the *B. rodhaini* Japan strain. The second major group is comprised of BMN1-2, BMN1-3, BMN1-6, BMN1-7, BMN1-9, BMN1-13, BMN1-4, MN-10 and N1-21 from the *B. microti* MN1 strain, BmSA1 from the *B. microti* Gray strain, BmP32 from the *B. microti* Munich strain, MSA1 and MSA2 from the *B. rodhaini* Australia strain and Br-1, p25 and p26 from the *B. rodhaini* Japan strain. Beyond these, the proteins BMN1-17 and BMN1-20 are paralogs that are unrelated to any of the above groups, and likewise BMN1-15 is unrelated to any of these other proteins. Hence, it is strongly recommended that henceforth the BMN1 be treated as distinct groups as per their evolutionary relationships.

The analysis herein showed that BmR1_03g04855 from the *B. microti* R1 strain belongs to the first of the major groups (i.e. BMN1-10 and its relatives). *B. microti* R1 has a total of 10 members of this group. Analysis of these proteins shows that they are characterized by the presence of a conserved domain which might be present in one to five copies per protein, with a single copy in BmR1_03g04855. Secondary structure prediction based on an alignment of this domain showed that it contains an N-terminal region with eight conserved β-strands followed by a C-terminal region with multiple cysteines. The N-terminal region is likely to adopt a β-sandwich fold whereas the C-terminal region is likely to adopt a disulfide bond supported structure. Iterative sequence profile analysis identified proteins with a divergent version of this domain outside of *Babesia* in a group of secreted proteins in *Theileria*. While this family is expanded across *Theileria* (it is particularly abundant in the horse-parasitic species *T. equi*, about 460 members), it is present in fewer numbers in *T. annulata, T. orientalis, T. parva*. As it is present in both the piroplasms, this domain was named the piroplasm β-strand (PiβS) domain. Given that the PiβS family is inferred to have been ancestrally present in the piroplasms, it is likely that it has played an important role in host-parasite dynamics of the entire piroplasm lineage. Importantly, the phylogenetic analysis of the PiβS domain in the genus *Babesia* showed that its evolution is dominated by lineage-specific expansions. Notably, the versions in *B. rodhaini* appear to have radiated entirely independently of those from *B. microti*. Moreover, even within *B. microti*, clades exclusively or predominantly containing R1 strain or MN1 strain proteins were found.

BMR1_02g04285 is a hypothetical protein of 177 amino acid length with homologies to maltese cross form related protein (GenBank accession no. AB079857.1). The protein is potentially involved in cytoskeleton remodeling, which provides evidence for its localization to be on the cell surface.

This suggests that these antigens have been evolving at very short evolutionary distances via independent lineage-specific expansions. Such a pattern is a hallmark of an arms race with the host and has been observed before in the case of other apicomplexan surface proteins such as the rifin-like and the var/DBL1 superfamilies in *Plasmodium falciparum*, and the vir/yir superfamilies in *P. vivax/P. yoelii*. This suggests that the PiβS and BAHCS domain families are similarly likely to be expressed on the cell-surface at the interface with the host immune system. The dynamic evolution suggests that the lineage-specific expansions are a positively selected response against the host immunity targeting them.

Characterization of Recombinant *B. microti* Antigens

Figure 3:
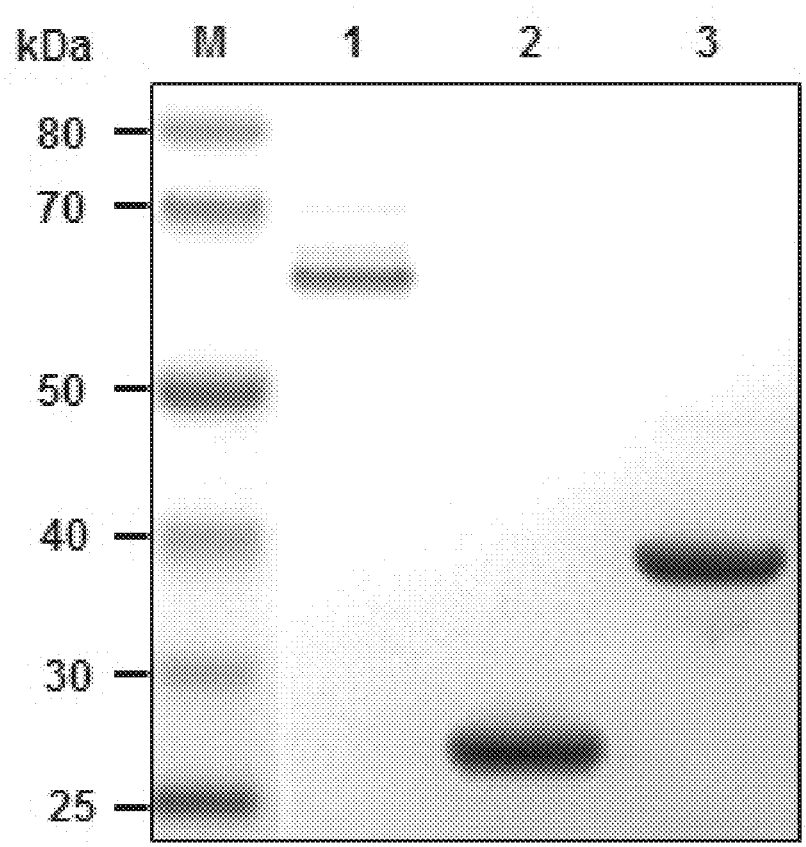
FIG. 3 shows SDS-PAGE analysis of His-tag purified, recombinant *B. microti* proteins BmSERA, BmMCFRP and BmPiβS. Proteins were separated on 4-12% SDS-PAGE gradient under reducing conditions and stained with Simply Blue Safestain. Lane M, molecular weight marker; Lane 1, BmSERA; Lane 2, BmMCFRP; Lane 3, BmPiβS.

The recombinant proteins BmSERA, BmPiβS and BmMCFRP consisted of 376, 252 and 177 amino acid residues, respectively, with an additional sequence to include the hexa-histidine tag and a spacer, resulting in calculated molecular weights of 44, 32 and 23 kDa, respectively. The cDNA and amino acid sequences of BmSERA, BmPiβS and BmMCFRP are shown below. Protein characterization was done on 4-12% sodium dodecyl sulfate-polyacrylamide gel electrophoresis (SDS-PAGE) following Coomassie blue staining (SimplyBlue SafeStain; Thermo Fisher Scientific, MA) (FIG. 3). Results showed that the purified proteins were highly pure with no visible contaminating bands. Recombinant BmMCFRP and BmPiβS demonstrated a gel mobility at the predicted molecular weight of ~25 kDa and ~35 kDa, respectively, on SDS-PAGE, whereas BmSERA showed a protein band at 65 kDa molecular weight. Protein mass spectrometry analysis of the purified recombinant B. microti proteins was performed to validate their identity. Results showed high sequence identity of the recombinant protein with the corresponding B. microti antigen.

```
BmSERA:
                                          (SEQ ID NO: 1)
GCTAAGCAGACTTTCATCAAAAACAAATCTCTCAC

TAATCCTGGCGTGGACAATCCGAACTTATCTGAAG

GAGTCGTTCCATCCGATGAACATATTTCTTCGCAA

TCCCAAATCCAACTTTTGAGCCCACTAGCAACACC

ATTTCAAGTGATACATCTCAACCAATCAACCAACC

AACCAATCAACCAACCAACCAATCAACCAGTCAAC

CAACCAACCAACCAATCAACCAACCAACCAACCAA

TCAACCAACCAACCAACCAACCAACCAATCAACCA

ACCAACCAACCAATCAACCAAACAACCAACCAACC

AACCAATCAACCAAACAACCAACCAACCAACCAGT

CAACCAATCAACCAACCAACCAATCAACCAATCAA

CCAAACAACCAAACAACCAACCAATCAACCAATCA

ACCAAACAACCAACCAACCAACCAGTCAACCAACC

AAACAACCAGTCAACCAACCAACCAACCAATCAAC

CAATCAACCAAACAACCAATCAACCAAACAACCAA

CCAACCAGTCAACCAACCAATCAACCAGTCAACCA

ACCAATCAACCAGTCAACCAACCAAACAACCAATC

AGTCAACCAACCAACCAATCAACCAATCAACCAAA

CAACCAACCAAACAACCAACCAACCAACCAAACAA

CCAAACAACCAACCAATCAACCAGTCAACCAACCA

AACAACCAATCAGTCAACCAATCAACCAACCAAAC

AATATAATGGGAGATAAGCGGGGCCTCAAAGGCGC

TGAAACCATGAGTCCTGCGCCCCTATTCGTTGAAG

TTGACATCCTGAAAGATTCTTTGGATAGTAACTTA

GAAGTATTATATCAAGTTAGTGTTAATGCTATTAT

GTTTGTCCGCGTCGCTAGAAACATGGCCTCAAACA

TCATAATTAAAAGTGTAAAGGTTGGAGAAGATATT

TTGTATTTAAATGATCGAAGACTTGACCTAATTCT

TGAATTTACAGTTACTTCTCAACAGGGTTTCCATA

TGAGGATCTACAATAATGATGATCGTACGGAGAAT

GGTGTTATCGGCTTTCTTTGTTCTTTCATAGTTGC

AGATCATATTCCTAAGTGGTACAATCCACCTAACT

CACGCCGT
```

```
                                          (SEQ ID NO: 2)
AKQTFIKNKSLTNPGVDNPNLSEGVVPSDEHISSQ

SQIQLLSPLATPFQVIHLNQSTNQPINQPTNQPVN

QPTNQSTNQPTNQPTNQPTNQSTNQPTNQPNNQPT

NQSTKQPTNQPVNQSTNQPINQSTKQPNNQPINQS

TKQPTNQPVNQPNNQSTNQPTNQPINQTTNQPNNQ

PTSQPTNQPVNQPINQSTNQTTNQSTNQPINQSTK

QPTKQPTNQPNNQTTNQSTSQPTKQPISQPINQPN

NIMGDKRGLKGAETMSPAPLFVEVDILKDSLDSNL

EVLYQVSVNAIMFVRVARNMASNIIIKSVKVGEDI

LYLNDRRLDLILEFTVTSQQGFHMRIYNNDDRTEN

GVIGFLCSFIVADHIPKWYNPPNSRR

BmMCFRP:
                                          (SEQ ID NO: 3)
TGTGATGATATTGGTAGGGCTAATCATAACCCCAA

TATACATAACTATCCCGCATTTTTAGAACCGATAG

ACATCGACATAAAGTCCACACCAGTACCGAAGGAT

GTTGAGTTTGACAACGGTGTTTTTAAGTTAGCTGG

TAGTCGCAAGACGGAATTGAAACTCAGACCAAAAG

TTGGGGGCAAGTACTTGGAGGTCTCTCCTCATGTT

GCCGTCGTTCAAGTTTCCGTTTCCGTTTCCGATGG

AATAATAAACGTCTACGAAGATGACTACCACAAAA

TTACTGTGAAGCAATTCGACATGGATGGGAATATC

ATTATTAAACAAAGGGAAGGTGCAATTTCGGCTCA

TCCATTTGCACAATTGGCATTCTCTGTTGCATCAT

CTGCAAACAATGTTATTTTAGAGGAAAATGAAATC

TTAAAGAAGAATATTCTCGAAGATAACAAAGATAA

TAGTCAATCAGACGGGGAAATTGCTTCTGAACAAG

AAAAAACTAGCACTTTATCATTCCCATCATCGCCA

TCATCA (SEQ ID NO: 4)
CDDIGRANHNPNIHNYPAFLEPIDIDIKSTPVPKD

VEFDNGVFKLAGSRKTELKLRPKVGGKYLEVSPHV

AVVQVSVSVSDGIINVYEDDYHKITVKQFDMDGNI

IIKQREGAISAHPFAQLAFSVASSANNVILEENEI

LKKNILEDNKDNSQSDGEIASEQEKTSTLSFPSSP

SS

BmPiβS:
                                          (SEQ ID NO: 5)
CCATCAAATGGCCTCTATGAATCTAACCTTTTTA

CACGGAAGGTTATGGCAAATATTTGACTAGTCCGA

CTAAGATAAAGACAATTGAATTTGGAGGTTATAAA

TTCGAGTTTGATGATGATACATTGCCTGTAACATC

TATAACAAAAATCGATGTAATAACATATGATGATA
```

```
                                                                (SEQ ID NO: 6)
AACCGATTTTATTTGAATTTATTTCAGATAAGGAT

CGTCCATACAGAAGATTTTACTACTATACTTTGGA

TAGTAAAACTAATAAATTATATAATTATGTCACTG

CAGAAACTGGATATAATGTTGAGGATTCGAGTGGT

CTAAAATACTACACTGAATTAAGTAAATCGGGAAT

AAATGATGTTTTACAAGATTTGGATAAAAACATTG

ATGAAAGTAATATCGAGCATTTGAAGACATCATAT

GTAACAAAAGGATTAAATATTGCGATTGAAGTTTA

TTCAAACAGAGTCGTTGAACAAATTAAATCGATAA

AGGTAGTTACTCCAGTTGAATTATTCGATTATAAA

ACTGAAGTTCCAATTGAGTCTGTAGATCATGAATC

GCGTGATAATTCATTGGCCGAAGTAGAGGAGGATG

GAAAAGCTGTACAAGTTGGGACTCAACCTGTGTAT

GAGGTAAATGATGGTGCTCATAACCCATCTGCACA

AGTGTTATCACAGAATAATATTATTGAGACCTTGG

ATGATAAATCTAAAGTTACTCATTTGAGAAATGCT

GGCAGTGAGAAAATTCGTGTT
```

```
                                             (SEQ ID NO: 6)
PSNGLYESNLFYTEGYGKYLTSPTKIKTIEFGGYK

FEFDDDTLPVTSITKIDVITYDDKPILFEFISDKD

RPYRRFYYYTLDSKTNKLYNYVTAETGYNVEDSSG

LKYYTELSKSGINDVLQDLDKNIDESNIEHLKTSY

VTKGLNIAIEVYSNRVVEQIKSIKVVTPVELFDYK

TEVPIESVDHESRDNSLAEVEEDGKAVQVGTQPVY

EVNDGAHNPSAQVLSQNNIIETLDDKSKVTHLRNA

GSEKIRV
```

ELISA Evaluation of *B. microti* Recombinant Antigens

Figure 4:
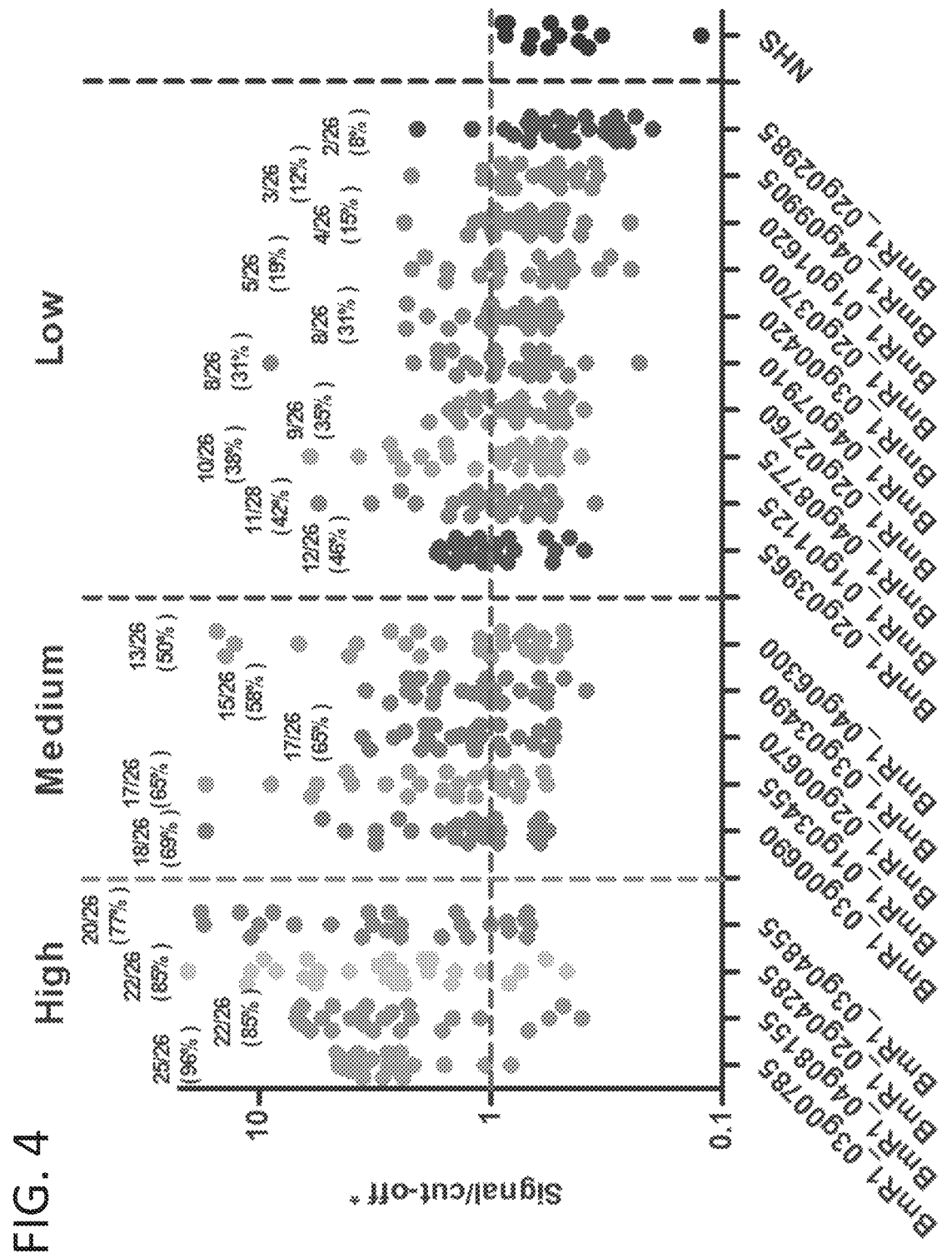
FIG. 4 is a graph showing the results of a *Babesia microti* enzyme-linked immunosorbent assay (BmELISA) to determine the sensitivity of *B. microti* proteins.

To evaluate the immunodominant antigens identified through phage display as potential screening markers for babesia, ELISA reactivity of the recombinant proteins against *B. microti*-infected sera was assessed. Table 1 shows ELISA screening results against sera from patients with clinical babesiosis and from healthy individuals on plates coated individually with 19 recombinantly purified immunodominant *B. microti* antigens. The pattern of reactivity of these antigens are different and not a single antigen is able to detect all of the clinical sera (FIG. 4). The sensitivity of the antigens varied and allowed specific classification of the antigens according to the number of clinical samples recognized. The three highest reactivity antigens were combined in a single well following an extensive standardization experiment to establish the coating concentration of an individual antigen without loosing the sensitivity of an individual antigen in combination. A total of 28 babesiosis patient sera were used to determine the sensitivity of ECL-BmELISA against BmSERA, BmMCFRP and BmPiβS antigens and combination antigens in detection of *B. microti* antibodies in serum samples. The following ELISA results were obtained: BmSERA: 93%; BmMCFRP: 75%; and BmPiβS: 73%. When a combination of the 3 antigens were used 27/28 (96%) of serum samples were found positive for *B. microti* antibodies (Table 2). These results showed that combining multiple antigens in a single well enhanced the sensitivity and robustness of *B. microti* antibody detection by ECL-BmELISA. For specificity determination, serum samples from 15 United States blood donors were tested in ECL-BmELISA against individual BmSERA, BmMCFRP and BmPiβS and a combination of the 3 antigens. As shown in the Table 2, all 15 of the serum samples (100%) were negative in ECL-BmELISA using either three individual or combination antigens.

TABLE 1

Results of BmELISA assay to determined the sensitivity of *B. microti* proteins

| Antigen | Number of human serum samples | |
|---|---|---|
| | *Babesia microti* positive | Normal human serum |
| BmBAHCS (BmR1_03g00785) | 27/28 (96%) | 0/15 |
| BmSERA (BmR1_04g08155) | 24/28 (86%) | 0/15 |
| BmMCFRP (BmR1_02g04285) | 23/28 (82%) | 0/15 |
| BmPiβS (BmR1_03g04855) | 22/28 (79%) | 0/15 |
| BmEGF (BmR1_03g00690) | 19/28 (68%) | 0/15 |
| BmR1_01g03455 | 19/28 (68%) | 0/15 |
| BmR1_02g00670 | 19/28 (68%) | 0/15 |
| BmR1_03g03490 | 17/28 (61%) | 0/15 |
| BmR1_04g06300 | 16/28 (57%) | 0/15 |
| BmR1_02g03965 | 14/28 (50%) | 0/15 |
| BmR1_01g01125 | 13/28 (46%) | 0/15 |
| BmR1_04g08775 | 12/28 (43%) | 0/15 |
| BmR1_02g02760 | 11/28 (39%) | 0/15 |
| BmR1_04g07910 | 10/28 (36%) | 0/15 |
| BmR1_03g00420 | 10/28 (36%) | 0/15 |
| BmR1_02g03700 | 8/28 (29%) | 0/15 |
| BmR1_01g01620 | 6/28 (21%) | 0/15 |
| BmR1_04g09905 | 5/28 (18%) | 0/15 |
| BmR1_02g02985 | 4/28 (14%) | 0/15 |

TABLE 2

ECL-BmELISA assay sensitivity and specificity

| Antigen | Number of human serum samples | |
|---|---|---|
| | *Babesia microti* positive | Normal human serum |
| BmSERA | 25/28 (89%) | 0/15 |
| BmMCFRP | 19/28 (68%) | 0/15 |
| BmPiβS | 20/28 (71%) | 0/15 |
| BmSERA + BmMCFRP + BmPiβS | 27/28 (96%) | 0/15 |

Nucleotide Diversity

To determine whether the three chosen molecules (BmSERA, BmPiβS and BmMCFRP) are strongly conserved and represent appropriate diagnostic targets, studies were performed to determine the nucleotide diversity naturally existing in the population. To achieve this, alignments were generated of nucleotide sequences from 41 samples (available on Piroplasmadb.org), including 36 human *B. microti* clinically infected cases, two samples from infected Ixodus ticks and four from infected rodents, and then compared to the laboratory adapted *B. microti* Peabody strain (used for phage library construction and gene cloning in the current study) that was isolated in Nantucket in 1973 for the determination of nucleotide and amino acid polymorphisms (Lemieux et al., *Nat Microbiol* 1(7):16079, 2016). The full length BmSERA, BmPiβS and BmMCFRP have a total of 130, 37 and 35 SNPs (single nucleotide polymorphisms) with non-synonymous to synonymous substitution ratio (dN/dS) of 3.06, 1.64 and 3.38, respectively. However, for the present study, only the immunodominant region of these proteins were cloned, calculated based on the theoretical antigenicity index, which has comparatively lowered the nucleotide variation to 46, 18 and 35 SNPs and dN/dS ratio of 2.5, 1.6 and 1.3 respectively, for BmSERA, BmPiβS and BmMCFRP. The nucleotide variation reported here as SNPs are mostly due to the *B. microti* Russia-1995 strain, which is reported to be highly variable at the genomic level relative to the strains isolated from the continental United States (Lemieux et al., *Nat Microbiol* 1(7):16079, 2016).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated complementary DNA (cDNA) encoding a *Babesia microti* antigenic polypeptide, wherein the amino acid sequence of the *B. microti* antigenic polypeptide consists of SEQ ID NO: 4.

2. The isolated cDNA of claim 1, consisting of SEQ ID NO: 3.

3. A vector comprising the isolated cDNA of claim 1, operably linked to a heterologous promoter.

4. A vector comprising the isolated cDNA of claim 2, operably linked to a heterologous promoter.

5. A vector comprising a complementary DNA (cDNA) encoding a *Babesia microti* antigenic polypeptide operably linked to a heterologous promoter, wherein the amino acid sequence of the *B. microti* antigenic polypeptide comprises no more than 5 conservative amino acid substitutions relative to SEQ ID NO: 4.

6. The vector of claim 5, wherein the amino acid sequence of the *B. microti* antigenic polypeptide comprises SEQ ID NO: 4.

7. The vector of claim 5, wherein the amino acid sequence of the *B. microti* antigenic polypeptide comprises no more than 2 conservative amino acid substitutions relative to SEQ ID NO: 4.

8. The vector of claim 5, wherein the nucleic acid sequence of the cDNA comprises SEQ ID NO: 3.

9. The vector of claim 5, wherein the nucleic acid sequence of the cDNA consists of SEQ ID NO: 3.

10. An isolated host cell comprising the vector of claim 5.

11. The isolated host cell of claim 10, wherein the cell is a bacterial cell.

12. The isolated host cell of claim 11, wherein the bacterial cell is *Escherichia coli*.

13. An isolated complementary DNA (cDNA) encoding a *Babesia microti* antigenic polypeptide, wherein the isolated cDNA consists of SEQ ID NO: 1.

14. A vector comprising the isolated cDNA of claim 13, operably linked to a heterologous promoter.

15. An isolated host cell comprising the vector of claim 14.

16. The isolated host cell of claim 15, wherein the cell is a bacterial cell.

17. The isolated host cell of claim 16, wherein the bacterial cell is an *Escherichia coli* cell.

\* \* \* \* \*